(12) United States Patent
Komala et al.

(10) Patent No.: US 10,671,202 B2
(45) Date of Patent: Jun. 2, 2020

(54) TOUCH MEASUREMENT APPARATUS AND METHOD OF USE

(71) Applicant: Mendology, Inc., Rio Rancho, NM (US)

(72) Inventors: Sarah E. Komala, Rio Rancho, NM (US); Eric M. Komala, Rio Rancho, NM (US)

(73) Assignee: Mendology, Inc., Rio Rancho, NM (US)

( * ) Notice: Subject to any disclaimer, the term of this patent is extended or adjusted under 35 U.S.C. 154(b) by 0 days.

(21) Appl. No.: 15/963,026

(22) Filed: Apr. 25, 2018

(65) Prior Publication Data

US 2018/0307362 A1 Oct. 25, 2018

Related U.S. Application Data

(60) Provisional application No. 62/556,202, filed on Sep. 8, 2017, provisional application No. 62/489,748, filed on Apr. 25, 2017.

(51) Int. Cl.
*G01L 1/00* (2006.01)
*G06F 3/041* (2006.01)
(Continued)

(52) U.S. Cl.
CPC ............ *G06F 3/0414* (2013.01); *A61B 5/00* (2013.01); *G01L 1/14* (2013.01); *G01L 1/16* (2013.01);
(Continued)

(58) Field of Classification Search
CPC .... G06F 3/0414; G06F 3/011; G06F 3/03547; A61B 5/00; G01L 1/14; G01L 1/16;
(Continued)

(56) References Cited

U.S. PATENT DOCUMENTS 3,658,550 A 4/1972 Hawley
3,802,220 A 4/1974 Pompo
(Continued)

FOREIGN PATENT DOCUMENTS

CN 102973409 3/2013
CN 103809781 5/2014
(Continued)

OTHER PUBLICATIONS

Strickland, Jonathan, "How Massage Chairs Work", https://electronics.howstuffworks.com/gadgets/home/massage-chair4.htm [Downloaded Aug. 2, 2017].

*Primary Examiner* — Max H Noori
*Assistant Examiner* — Masoud H Noori
(74) *Attorney, Agent, or Firm* — Peacock Law P.C.; Justin R. Jackson; Philip D. Askenazy

(57) ABSTRACT

An apparatus and method for measuring a manual force that uses a pad that simulates human or animal body tissue and a sensor configured to receive the force. The pad can have the shape of a body part and can have different materials that have different hardnesses. The apparatus can have interchangeable pads and identify individual users for training purposes, such as for training massage therapists. The apparatus can indicate whether an applied force is within a predetermined range. Also a method of defining a standard or protocol for training and/or performing touch manipulations by applying a range force to one or more persons with an algometer and establishing a protocol based on data obtained from biosensors attached to the person in order to determine which forces produce a desired effect, such as a reflexive, mechanical, or relaxation effect. The apparatus can then be used to train a provider on how to follow the standard or protocol. Also a method of controlling environmental conditions using data from one or more biosensors attached to a person to adjust an environmental condition (Continued)

such as room temperature or lighting in order to achieve a desired effect in the person. Also a method and apparatus of training a person to perform an activity that requires producing a force in a certain way, such as performing bicycle tricks or kneading dough. The apparatus can be shaped to simulate an object related to the activity.

37 Claims, 28 Drawing Sheets

(51) Int. Cl.
| | |
|---|---|
| H03K 17/96 | (2006.01) |
| G02B 27/01 | (2006.01) |
| G01L 1/14 | (2006.01) |
| G06F 3/0354 | (2013.01) |
| G01L 1/20 | (2006.01) |
| G01L 1/16 | (2006.01) |
| A61B 5/00 | (2006.01) |
| G09B 5/06 | (2006.01) |
| G06F 3/01 | (2006.01) |
| G09B 23/30 | (2006.01) |

(52) U.S. Cl.
CPC ............ *G01L 1/20* (2013.01); *G02B 27/0172* (2013.01); *G06F 3/011* (2013.01); *G06F 3/03547* (2013.01); *G09B 5/06* (2013.01); *G09B 23/30* (2013.01); *H03K 17/9625* (2013.01)

(58) Field of Classification Search
CPC ......... G01L 1/20; G02B 27/0172; G09B 5/06; G09B 23/30; H03K 17/9625
USPC ...................................................... 73/862.68
See application file for complete search history.

(56) References Cited

U.S. PATENT DOCUMENTS

| | | | |
|---|---|---|---|
| 4,140,997 A | 2/1979 | Brady | |
| 4,729,368 A | 3/1988 | Guitay | |
| 5,053,341 A | 10/1991 | Companion | |
| 5,211,976 A | 5/1993 | Cox et al. | |
| 5,633,286 A | 5/1997 | Chen | |
| 5,807,288 A | 9/1998 | Wu | |
| 6,230,574 B1 | 5/2001 | Rider et al. | |
| 6,232,366 B1 | 5/2001 | Wang et al. | |
| 6,645,161 B2 | 11/2003 | Koenig et al. | |
| 6,877,178 B2 | 4/2005 | Chapman et al. | |
| 7,272,766 B2 | 9/2007 | Sakezles | |
| 7,517,327 B1 | 4/2009 | Knight | |
| 8,414,908 B2 | 4/2013 | Jin et al. | |
| 8,735,117 B2 | 5/2014 | Dalring et al. | |
| 8,915,742 B2 | 12/2014 | Hendrickson et al. | |
| 9,138,370 B2 | 9/2015 | Taskinen et al. | |
| 9,472,123 B2 | 10/2016 | Trotta et al. | |
| 9,514,658 B1 | 12/2016 | Hart et al. | |
| 2004/0028112 A1* | 2/2004 | Carlsson | G01K 17/006 374/36 |
| 2004/0260215 A1 | 12/2004 | Kim | |
| 2006/0071286 A1* | 4/2006 | Axelrod | G01N 29/036 257/414 |
| 2007/0027542 A1 | 2/2007 | Xu | |
| 2007/0209497 A1 | 9/2007 | Robertson | |
| 2008/0009687 A1* | 1/2008 | Smith | A61B 5/0002 600/302 |
| 2008/0032274 A1 | 2/2008 | MacNamara et al. | |
| 2010/0311025 A1 | 12/2010 | Everett | |
| 2012/0226197 A1 | 9/2012 | Sanders et al. | |
| 2012/0265107 A1 | 10/2012 | Smith | |
| 2013/0109997 A1* | 5/2013 | Linke | G06F 19/3418 600/549 |
| 2014/0186809 A1 | 7/2014 | Hendrickson et al. | |
| 2014/0207292 A1 | 7/2014 | Ramagem et al. | |
| 2015/0011921 A1 | 1/2015 | Sidhu | |
| 2015/0018968 A1 | 1/2015 | Sun et al. | |
| 2015/0105688 A1 | 4/2015 | Ross | |
| 2015/0119771 A1 | 4/2015 | Roberts | |
| 2015/0216683 A1 | 8/2015 | Laghi et al. | |
| 2015/0313542 A1* | 11/2015 | Goldberg | A61B 5/0205 600/384 |
| 2016/0270671 A1* | 9/2016 | Madabushi | G01C 23/00 |
| 2016/0361556 A1 | 12/2016 | Pearce et al. | |
| 2016/0381789 A1* | 12/2016 | Rogers | H01L 21/8258 361/749 |
| 2017/0079871 A1 | 3/2017 | Zhang | |

FOREIGN PATENT DOCUMENTS

| | | |
|---|---|---|
| CN | 205814888 | 12/2016 |
| GB | 2416127 | 1/2006 |
| WO | 0036577 | 6/2000 |
| WO | 2009146142 | 12/2009 |
| WO | 2016134269 | 8/2016 |

* cited by examiner

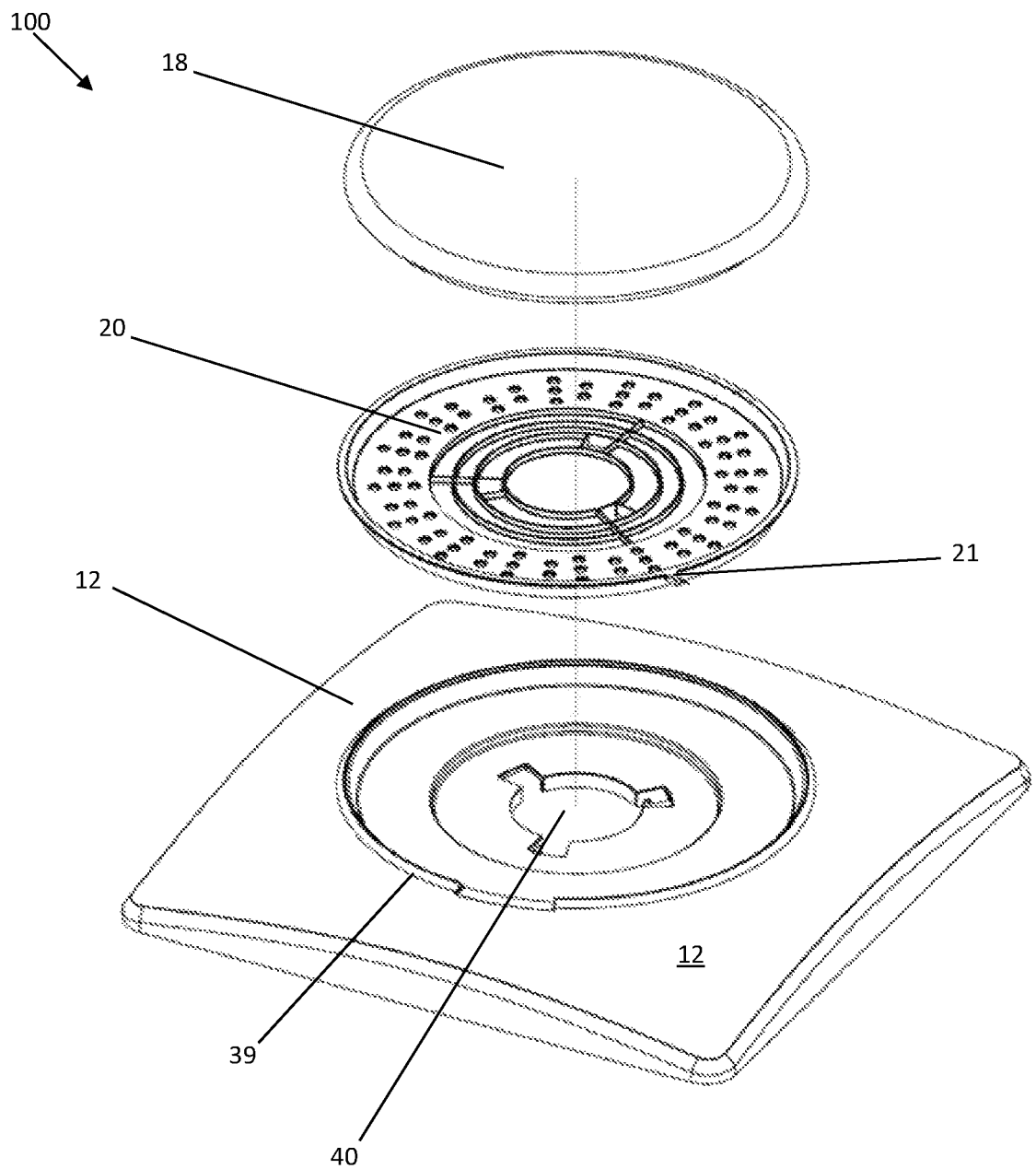

TOUCH MEASUREMENT APPARATUS AND METHOD OF USE

CROSS-REFERENCE TO RELATED APPLICATIONS

This application claims priority to and the benefit of the filing of U.S. Provisional Patent Application No. 62/489,748, entitled "System to Define and Standardize Reflexive and Mechanical Effects of Manual Therapies", filed on Apr. 25, 2017, and U.S. Provisional Patent Application No. 62/556,202, entitled "Touch Measurement Apparatus and Method of Use", filed on Sep. 8, 2017, and the specifications and claims thereof are incorporated herein by reference.

BACKGROUND OF THE INVENTION

Field of the Invention (Technical Field)

Embodiments of the present invention relate to apparatuses, systems, and methods that use pressure, acceleration, torque, torsion, velocity, mass, force, friction, kinetic energy, tilt and position measuring sensors, and biosensors to define reflexive and mechanical effects of manual therapy and to standardize training and delivery of those effects.

DESCRIPTION OF RELATED ART

Massage and manual therapy manipulations apply pressure and force to bodily structures to create a physiological effect. The pressure and force used to produce a relaxation effect are different from those used to produce an effect for pain and mobility reasons. The industry has not defined the pressures and forces that create these different effects, thus creating subjective delivery of manual manipulations.

The effects of massage and manual therapy are classified into two categories, reflexive and mechanical. Reflexive effects are those that create a change to the nervous system. Mechanical effects are those that create a change to soft tissue, including muscles, tendons and connective tissue.

Massage manipulations that create reflexive or mechanical effects are currently defined as light pressure, moderate pressure, heavy pressure, firm pressure, deep pressure, soft pressure, gentle pressure, and more. The general consensus within the industry is that the "lighter" the pressure, the more reflexive, and the "deeper" the pressure, the more mechanical. The problem is that these terms are subjective. Pressure is defined by the personal characteristics of each student and massage therapist or manual therapist providing the protocol. While the massage therapy industry creates "protocols", which are defined sets of techniques, modalities, protocols etc. for a complete treatment or for a particular manipulation, the industry has not created a standard for measuring manual force applied during treatment.

Muscle tissue varies from person to person making it difficult to create exact definitions for massage manipulations including what constitutes light, moderate or firm, heavy or deep pressure and the effects they create. Setting ranges for these manipulations is still beneficial for removing subjectivity and creating a consistent standard in massage therapy education, service standards and quality service delivery.

Training massage therapists to be proficient in pressure manipulations allows them to have a foundation to perform massage therapy services with the best outcomes for the public. It also increases the quality and service standards of any clinic, spa, medical office or hospital. Embodiments of the present invention can be used to train, test, or evaluate the proficiency of both professionals and non-professionals in diverse fields that rely, at least partially, on the ability to provide a particular amount of force to a living or inanimate object, including but not limited to painters, tattoo artists, sculptors, cooks, bakers, persons providing microdermabrasion treatments, etc.

Research studies that focus on massage therapy effects have been performed with inconclusive results. Each massage therapist has a subjective view on how to perform the manipulations in these studies. There is thus a present need for a method, apparatus, and system that removes subjectivity and creates a standard in massage therapy education and training so that consistent treatments, outcomes and research can be obtained, as well as to provide manual therapy and product application education and training for massage therapists as well as other professionals and non-professionals, like the general public.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention.

BRIEF SUMMARY OF EMBODIMENTS OF THE PRESENT INVENTION

The present invention is a manual force measurement apparatus comprising a base, a pad disposed on the base comprising a material that simulates human or animal body tissue, and at least one sensor configured to receive a force applied by a person, the at least one sensor capable of generating output data related to the force. The apparatus preferably further comprises a display for displaying the output data. The display preferably comprises a device selected from the group consisting of optical projection system, monitor, handheld computing device, head-mounted display, head-up display, and smart glasses. The pad is preferably removeable from the base. The pad optionally comprises materials having different hardnesses, at least one of the materials preferably comprising at least one object selected from the group consisting of beads, marbles, spheres, strips and tubes. The pad optionally comprises a pocket for receiving an ice pack, and the pad may optionally comprise a material having a lower freezing point than water. The pad preferably comprises a shape selected from the group consisting of an anatomical body part of a human or animal, a sphere, a square, and a triangle. The pad optionally comprises a pressure-sensitive conductive sheet. The apparatus preferably further comprises a radio frequency identification reader or an identification card scanner, and preferably further comprises a recognition device for recognizing a fingerprint or personal identification number. The apparatus preferably further comprises a wireless connection between the at least one sensor and the base and preferably further comprises a wireless transmitter for transmitting the output data.

The present invention is also a method of measuring a manual force, the method comprising a pad receiving a manually applied force, wherein the pad comprises a material that simulates human or animal body tissue, and generating data related to the applied force using at least one sensor. The method preferably further comprises displaying the data, storing the data, and/or transmitting the data to another device or network. The method preferably further comprises producing a sound or visual effect when a predetermined force is applied. The method optionally further comprises performing the receiving and generating steps at the beginning of a time period, repeating the receiving and generating steps at the end of a time period, and comparing the data from each time period. The method preferably further comprises associating a value of the applied force with a preexisting standard or protocol and/or indicating whether or not the force is within a predetermined range. The method optionally further comprises disposing an ice pack on or within the pad and freezing the pad. The method preferably further comprises identifying an individual user of the pad.

The present invention is also a method of defining a standard or protocol for training and/or performing touch manipulations, the method comprising attaching a biosensor to a person, applying different forces to the person using an algometer, obtaining data from the biosensor during the applying step; determining a range of forces that produce a desired effect in the person as measured by the data; and using the range of forces to establish a standard or protocol to produce the desired effect. The desired effect preferably comprises an effect selected from the group consisting of parasympathetic nervous system response, reflexive effect, fluid exchanges in soft tissue, mechanical effect, and relaxation effect. The standard or protocol is preferably established based on data obtained from performing the attaching, applying, obtaining, and determining steps on a plurality of persons. The method preferably further comprises instructing a user to apply a force to a pad, wherein the pad comprises material that simulates human or animal body tissue and wherein the pad generates user force data using at least one sensor, comparing the user force data to the standard or protocol, and repeating the instruction step until the user has satisfied a predetermined accuracy related to the protocol.

The present invention is also a method of using biosensors to control environmental conditions, the method comprising attaching a biosensor to a person, obtaining data from the biosensors, the data based on a force applied by a provider to the person's body; and using the data to adjust an environmental condition. The environmental condition is preferably selected from the group consisting of: temperature of a room, temperature of a table, room light intensity, room light color, sound volume, music selection, aromatherapy type, and aromatherapy intensity. The environmental condition is preferably automatically adjusted based on the data. The method preferably further comprises displaying the data to the provider so the provider can adjust the force applied to the person. The provider is preferably a manual or massage therapist and the method is used as an adjunctive or diagnostic tool.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 8B is a drawing that illustrates an exploded perspective view from above of a touch measurement apparatus according to an embodiment of the present invention;

DETAILED DESCRIPTION OF THE INVENTION

Figure 1A:
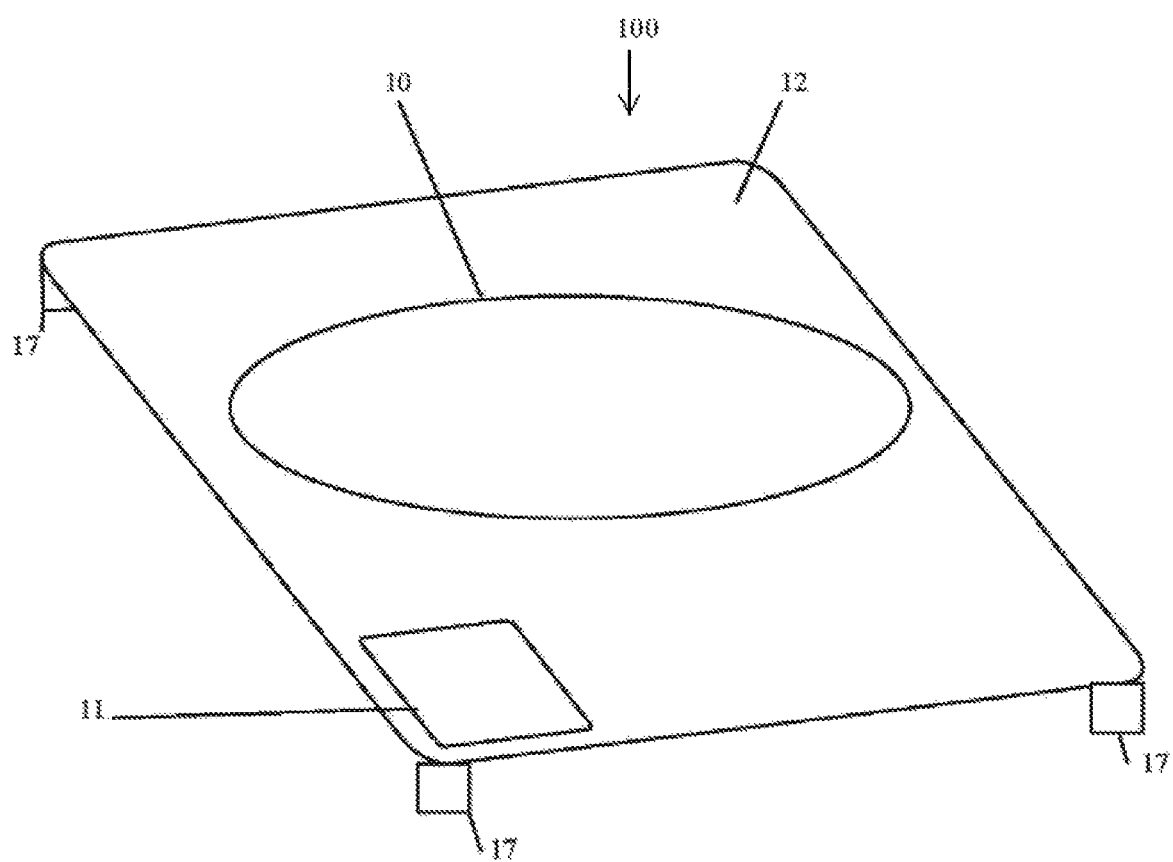
FIG. 1A is an elevated top perspective view drawing that illustrates a touch measurement apparatus according to an embodiment of the present invention with a palpation area, output display and housing base.
Figure 1B:
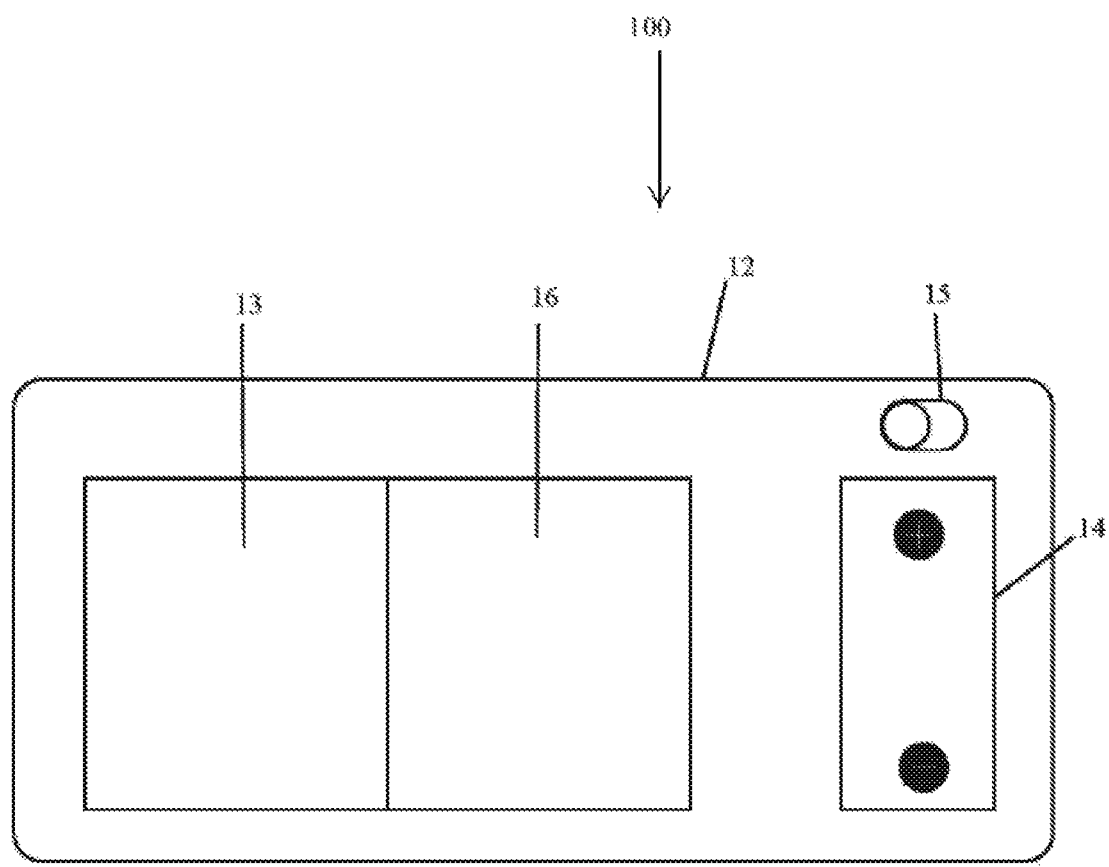
FIG. 1B is a bottom view drawing that illustrates a processing unit and electrical circuitry, electric supply, and on/off switch according to an embodiment of the present invention.

Embodiments of the present invention relate to a method, apparatus and system for standardized touch in manual therapies that can deliver any manipulation, with the same pressure, every time on every consumer. Embodiments of the present invention allow a standardized delivery of any manual therapy protocol or manipulation in the field of massage, spa services, personal training, physical therapy, occupational therapy, chiropractic, veterinary, dentistry, sports medicine and other fields that use manual manipulation. The present invention can also be used in the health and wellness, and pet owner consumer market. Embodiments of the present invention also increase quality and service standards with three steps, create pressure standards for any protocol, modality or technique, train the therapist, or person to deliver that set standard, and confirm proficiency of the therapist.

Embodiments of the present invention permit consumers to have a consistent experience no matter which therapist they see. This consistent experience increases client retention for such practitioners and businesses. Embodiments of the present invention can also reduce the chance of client loss when a therapist moves to another location or starts his/her own practice, thus increasing bookings for new therapists as consumers receive consistent service, no matter the therapist; increase treatment outcomes for services; and apply correct pricing for services performed (i.e., deep tissue vs. relaxation massage). Embodiments of the present invention can also be used to improve the use of a product or tool that is used on a person, animal, or inanimate object—including but not limited to spine and nervous system activators, micro-needling, permanent makeup and general tattoo artistry, compression garments, microdermabrasion and others.

Referring now to the figures, touch measurement apparatus (hereinafter called "touch trainer") 100 includes palpation area 10, output display 11 and base 12, as best illustrated in FIGS. 1A and 1B, 8A and 8B and 21A, 21B, 21C, and 21D. Palpation area 10 preferably includes pad 18, which is preferably disposed on and/or attached to base 12 with an adhesive or other attachment mechanism, fastener, or combination thereof and is electrically connected to processing unit 13 and electrical circuit board 16. Feet 17, which most preferably include a rubber or elastic or resilient bottom portion, but which can comprise any material of any shape or size sufficient to support touch trainer 100, are preferably attached to base 12 or can optionally be integrally formed into base 12 and most preferably reduce slipping. In one embodiment, feet 17 can optionally be formed by bending down or molding side extensions or legs from base 12.

Figure 2:
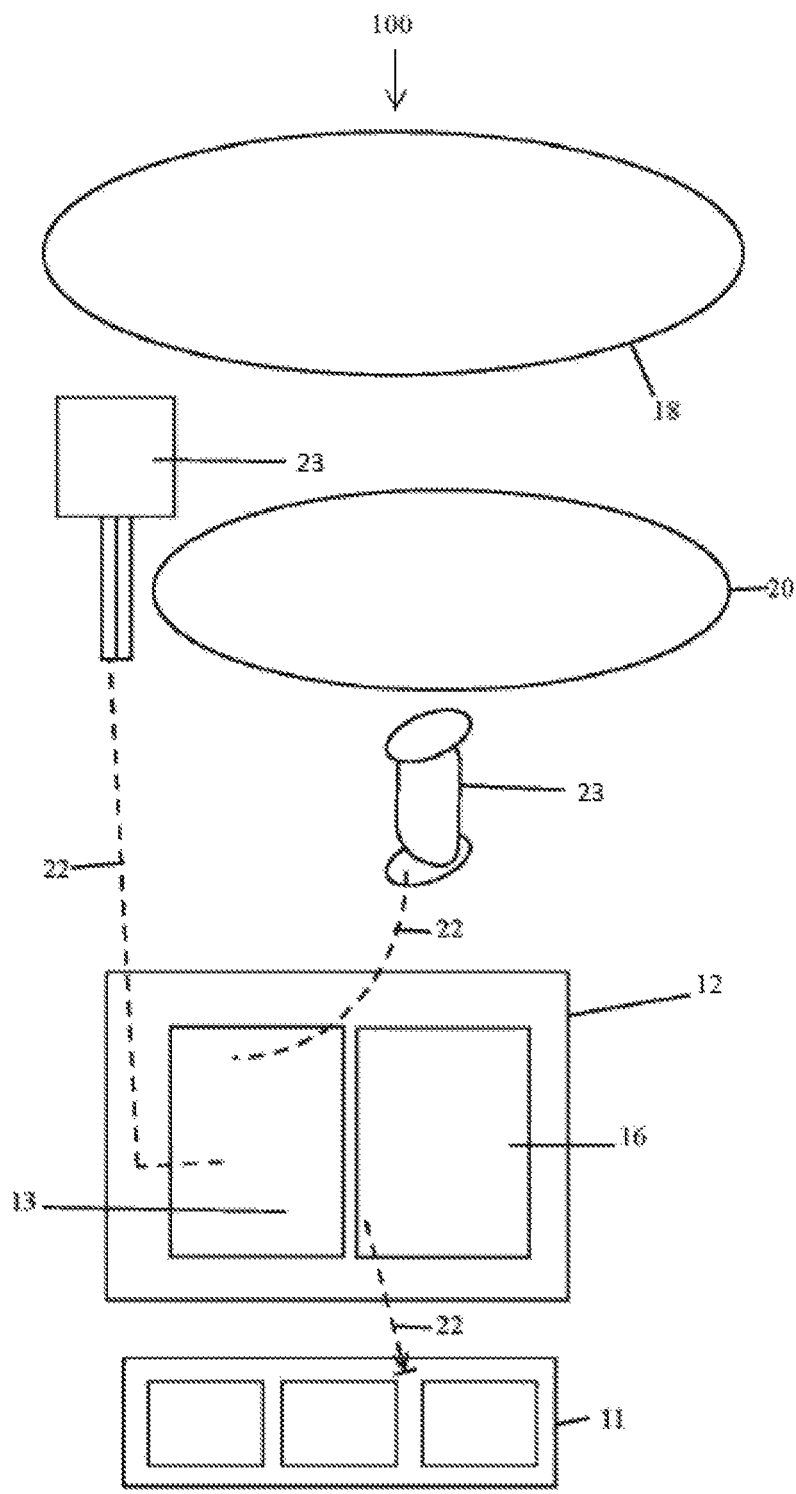
FIG. 2 is a drawing that illustrates a palpation area including pressure sensor and processing unit, electrical circuitry and output display according to an embodiment of the present invention.

As best illustrated in FIG. 2, palpation area 10 of touch trainer 100 preferably includes pad 18 that is preferably attached to or disposed on substrate 20 and communicably coupled with one or more force sensors 23, which in the embodiment illustrated in FIG. 2, includes a pressure sensor and a force sensitive receptor ("FSR"). The terms "force sensor" and "force sensitive receptor" are used interchangeably herein and thus discussions relating to either of the terms are equally applicable to both of the terms. As used throughout the specification and claims, the term "force" means force pressure, squeeze, acceleration, weight, torque, torsion, strain, stress, velocity, friction, kinetic energy, tilt, position, light pressure, moderate pressure, heavy pressure, firm pressure, deep pressure, soft pressure, gentle pressure, and the like. Embodiments of touch trainer 100 can comprise any of the following force sensors 23 and combinations thereof: telemetry sensors connected to a Cloud based system to collect use data and machine data or to connect to the Internet of Things (IOT); squeeze dynamometers; multi-axis accelerometers to detect magnitude, direction of the proper acceleration and to sense orientation because direction of weight changes, coordinate acceleration, vibration; position sensors like linear displacement sensors, tilt and inclinometers; piezo film sheets like Velostat, or other to track and confirm contacts, preferably added to the palpation pad 18 to monitor if whole hand is in contact with palpation pad or just a finger, etc. (if palpation pad 18 is in the form of, for example, a mannequin, it is preferable to track the contact and coverage area for the protocol, manipulation or technique being applied); pulse rotation sensors (multi-turn potentiometers, pulse encoders); static friction (before motion starts) and kinetic friction (in motion) sensors; radial force sensors (for example, if the speed of the object is changing, then there must also be a force in the direction of motion, which is tangential to the path); time measurement sensors; and kinetic energy sensors. In another embodiment, force sensors 23 can comprise a spring balance, electronic balance, strain gauge, or another mechanical force detection device which can sense and display a force. For example, a mechanism similar to or the same as that of a conventional bathroom, postal or kitchen scale can be used. In this embodiment, the display preferably comprises a mechanical display, including but not limited to a dial display. Alternatively or additionally, an electrical display can be used to display the output from the mechanical force detection device.

Substrate 20 can be formed from any rigid material, including but not limited to metal, plastic, wood, fiberglass, combinations thereof, and the like. In one embodiment, substrate 20 can optionally simply be a portion of base 12. In this embodiment, force sensor 23 can be disposed between base 12 and pad 18. Force sensor 23 can comprise one or more piezoelectric sensors, one or more stress strain gauges, and/or any other material or structure which is capable of altering an output based on a change in pressure applied thereto. Preferably, the pressure on each force sensor 23 is sampled at a rate no less than ten samples per second. Substrate 20 can comprise a resilient material and can optionally be formed into a three-dimensional shape that accommodates the attachment or operation of force sensors 23.

Base 12 is preferably made of impact resistant plastic, including but not limited to UB certified, a metal, or a combination thereof. Base 12 most preferably houses processing unit 13, electrical components 16, output display 11 and optionally power supply 14 for embodiments wherein power supply 14 comprises one or more batteries. Alternatively power supply 14 may comprise a receptacle for an electrical cord. Base 12 can be formed into any desired shape, including but not limited to round, square, tear drop shaped or other shape. Force sensors 23, as well as pad 18 and optionally substrate 20 can be connected remotely from base 12. For example, force sensor 23 can be disposed within a dummy or mannequin and connected wirelessly or via a wired connection to base 12. Base 12 can be finished with decorative vinyl, paint, stain or other finish and coated with an epoxy, decoupage or plastic. Base 12 can comprise power button 15 that engages power supply 14, preferably a non-latching push button. Base 12 can comprise a radio frequency identification ("RFID") reader 60, which, when used in coordination with a pad that comprises an RFID chip 62, can identify the individual pad and its data and associate it with a user of that pad. The RFID chipped pad allows a user to register themselves and see their use data. When used in an educational system, RFID indentured pads 18 allow educators to see the data of all students in class through a software system and can provide additional training and support to those that need it. Base 12 can also contain fingerprint recognition and/or personal identification number (PIN) capabilities to confirm the user's identity and protect the individual pad user's information and certification. This also allows an instructor to monitor all touch training devices at a glance and allows clinicians to become standard touch certified through a software program.

Pad 18 can include any material, but most preferably comprises a material that simulates human tissue, including but not limited to an elastomeric material including but not limited to thermoplastic elastomer, silicone, elastomer, polyurethane, marble, cork, combinations thereof, and the like. Pad 18 may comprise various embedded materials to simulate different tissues or objects, for example, marbles for trigger points and knots, rope for tendons, etc., various examples of which will be described further below.

Figure 22:
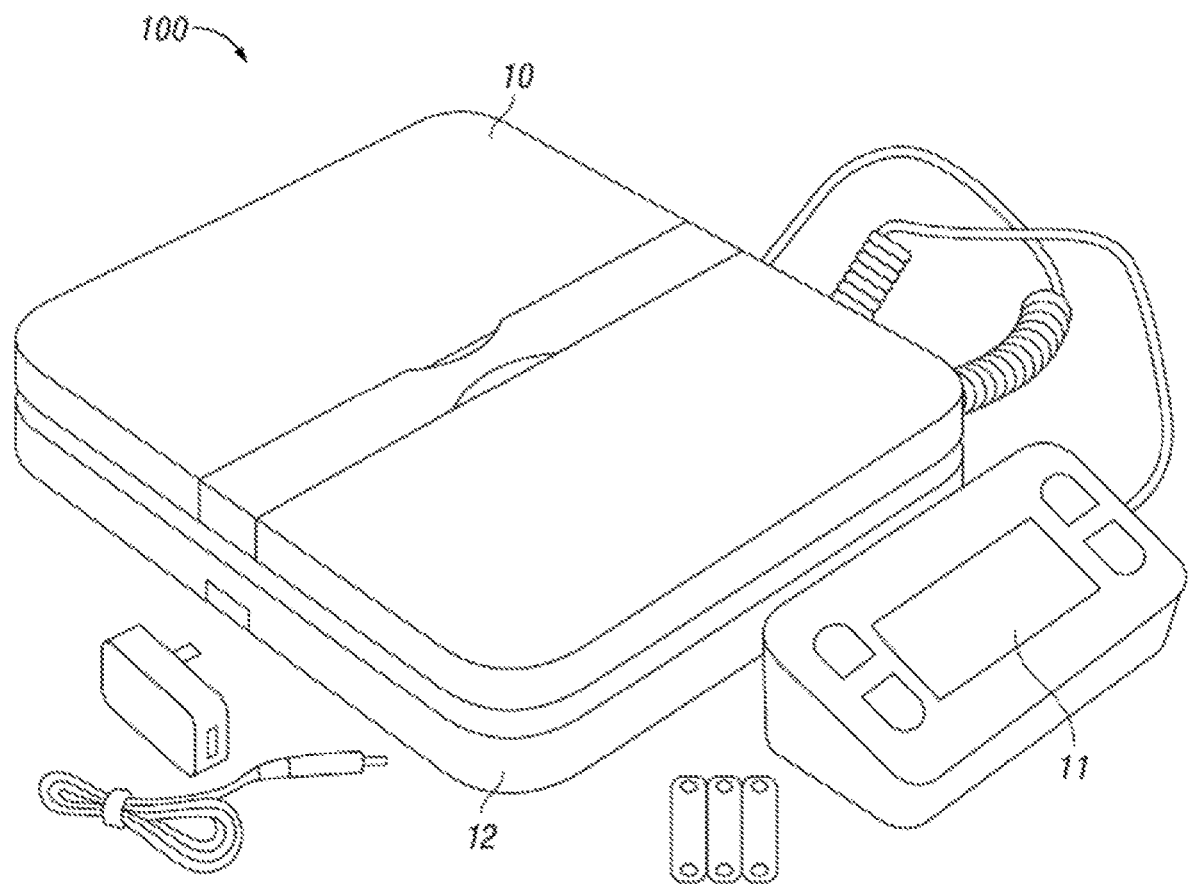
FIG. 22 is a drawing that illustrates a touch measurement apparatus according to an embodiment of the present invention comprising a base unit without a bezel or pad.

Pad 18 can be placed on substrate 20 and held in place merely by gravity. Substrate 20 can comprise a shape which accommodates pad 18 and which can optionally hold pad 18 with an interference fit. For example, substrate 20 can comprise a cupped shape into which a bottom portion of pad 18 can be held with an interference fit. Additionally, pad 18 can be secured to substrate 20, for example with an adhesive, one or more mechanical fasteners, suction cup, spring, hook and loop tape, combinations thereof and the like. Substrate 20 can have one or more projections disposed thereon and pad 18 can have one or more corresponding holes formed into a bottom thereof such that pad 18 can be secured to substrate 20. Of course, numerous other mechanical connections can be used and will provide desirable results. For example, an opening can be formed on a bottom portion of pad 18 and a threaded or ribbed member can extend up from bezel 39 and/or base 12. Another embodiment of touch trainer 100 has no pad 18 or bezel 39, as illustrated in FIG. 22, wherein palpation area 10 comprises a platform attached to base 12 through which at least one force sensor 23 such as an electronic balance takes data 26.

Force sensors 23 preferably comprise one or more electrical connections 22 that connect force sensors 23 to processing unit 13 and/or circuit board 16. Although processing unit 13 and circuit board 16 are illustrated in the drawings as being two different items, in another embodiment, they can be incorporated together as a single unit.

Touch trainer 100 is preferably powered by power supply 14, which can comprise one or more batteries, an alternating current source, and/or a direct current source. Data from force sensors 23 is preferably communicated to processing unit 13 via wireless connection 52 and/or wired connection 38, and preferably the storage of data 26 begins only after touch trainer 100 is activated by a user. Preferably, wired connection 38 comprises at least one USB port and line, but as described above, can be any wired data transmission line. Wireless connection 52 preferably comprises a Bluetooth system, but can be any type of wireless transmitter of data, including but not limited to wireless networking via WLAN or Wi-Fi, satellite, etc. Processing unit 13 communicates data 26 via wireless connection 52 and/or wired connection 38 to software application 280, which is preferably a web-based or cloud-based application or operating system. In the embodiment illustrated in FIG. 3, remote display 28 can optionally be connected to software application 280 to provide visual indication 29 of data 26. Preferably, data 26 will transfer when touch trainer 100 is plugged in and will be stored for future use in a cloud-based system like IBM, Microsoft Azure or other. Data 26 can also be stored in a removable data storage medium such as a USB thumb drive or micro-SD card, for example via a Serial Peripheral Interface (SPI) bus disposed on touch trainer 100. Data 26 can also be transferred from force sensors 23 to remote displays 28 or to Cloud data storage 53, preferably through wired connection 38 or wireless connection 52.

Figure 6:
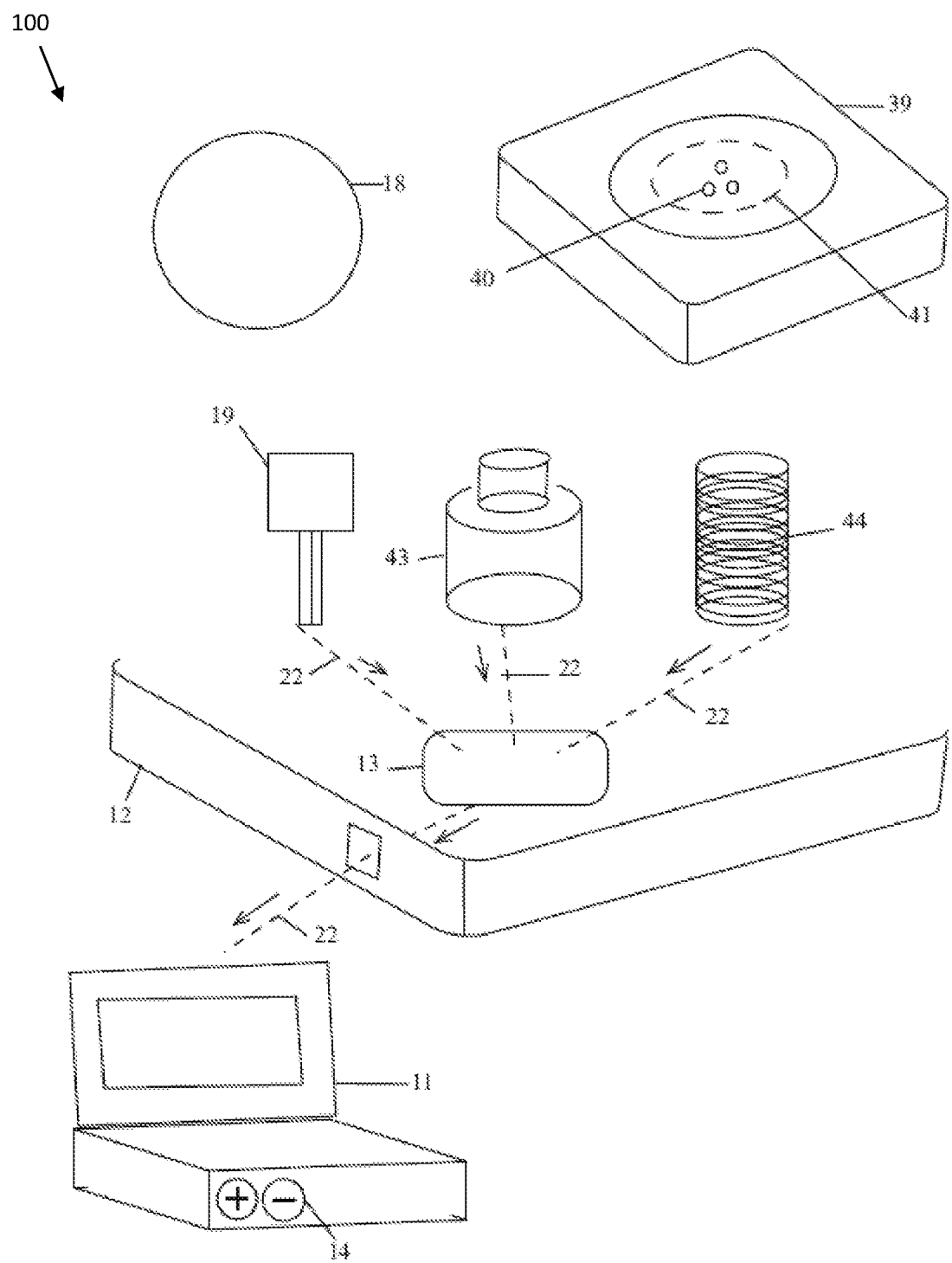
FIG. 6 is a drawing that illustrates various types of force sensitive receptors that can be used according to embodiments of the present invention.

In one embodiment, processing unit 13 sends the analyzed data to output display 11 which can comprise any visual display, including but not limited to a computer monitor, but which most preferably comprises an alphanumeric light-emitting diode display or liquid crystal display which is capable of displaying a numeric or graphical indication of the pressure and/or force being applied to pad 18. Output display 11 can optionally be remote from base 12 and is thus sometimes referred to herein as remote display 28. This output is generally referred to herein as the protocol force pressure reading ("PFPR") 33. Output display 11 can also be a touch-screen that preferably allows the user to set the PFPR range. Although in one embodiment, output display 11, which is most preferably an alphanumeric display, is preferably disposed on, attached to, or incorporated into base unit 12, in another embodiment one or more output displays 11 can optionally be a separate unit from base unit 12. In this embodiment, output display 11 can receive data via a wired and/or wireless connection to base unit 12. Alternatively, a first display can be disposed on, attached to, or incorporated into base unit 12 while a second display can be remotely connected thereto. As best illustrated in FIG. 6, a plurality of different types of force sensors 23 can be used individually and/or collectively in a single apparatus, including but not limited to FSR 19, load cell 43, and/or spring balance 44, all of which are referred to herein as force sensors 23. The results of these are preferably sent via electrical signals or connection 22 to processing unit 13, which then preferably sends the analyzed signals to output display 11, which itself can optionally comprise an internal and/or external power supply 14.

Output display 11 is preferably electrically coupled to processing unit 13, preferably via serial technology such as 12C/SPI or similar low-wire count implementations. Although FIG. 1A illustrates an embodiment wherein touch trainer 100 comprises a generally flat top surface, in one embodiment, touch trainer 100 can comprise any shape that permits a palpation area 10 and display 11 to be provided, including but not limited to: all or a portion of human anatomy, a sphere, a stone (e.g. basalt stone), a muscle; combinations thereof, and the like.

Preferably processing unit 13 is a microcontroller such as an STM32 microcontroller by STMicroelectronics. One or more processes of processing unit 13 can be performed by analog and/or digital electrical components, including digital logic units, comparators, micro controllers, microprocessors, and combinations thereof. Further, because processing unit 13 and circuit board 16 can be configured together as a single unit, throughout the application, when processing unit 13 is mentioned, it is to be understood that in an alternative embodiment, circuit board 16 can be used in conjunction with processing unit 13 and/or in lieu of processing unit 13. In addition, because processing unit 13 and circuit board 16 can be configured together as a single unit, throughout the application, when circuit board 16 is mentioned, it is to be understood that in an alternative embodiment, processing unit 13 can be used in conjunction with circuit board 16 and/or in lieu of circuit board 16. Preferably circuit board 16 is mounted inside touch trainer 100, has the capacity of supporting force sensors 23, which preferably includes at least one stress strain gauge and at least one force sensor, preferably to a maximum of twenty force sensors, and has the capability of programming processing unit 13, preferably via a USB port/lines. Preferably processing unit 13 has the ability to power down touch trainer 100 and prioritizes power from wired connection 38 over power from battery power supply 14. Preferably wired connection 38 comprises a Uniform Serial Bus line and port ("USB"), but embodiments of wired connection 38 can comprise other wired data and/or power connections including but not limited to standard power cords, FireWire, eSata, Thunderbolt, etc.

As force and pressure are applied to palpation area 10 of touch trainer 100, processing unit 13 analyzes the resulting electrical signal and sends data to output display 11, which displays the pressure and force—most preferably as a numeric value, or graphically, such as on a scale. Touch trainer 100 preferably comprises or is communicably couplable to power supply 14, which can optionally comprise a battery, an alternating current source, a direct current source, and/or a combination thereof. On/off switch 15 is preferably provided to disconnect power from power supply 14. The data for each user may be stored in memory of touch trainer 100 and/or transmitted to another device.

To use an embodiment of the present invention, a user preferably unpacks touch trainer 100, charges or installs batteries or plugs in the apparatus. The user then preferably turns on touch trainer 100 with switch 15. In those embodiments in which pad 18 is interchangeable with or removeable from the touch trainer 100, the user may need to insert pad 18 into touch trainer 100, as more thoroughly described elsewhere. For some embodiments, depending on the force sensors 23 used, it may be necessary to provide a short period of time for the apparatus to stabilize or to otherwise clear the apparatus in order to cause output display 11 to indicate a zero reading from the pressure sensors, such as is conventionally done on some digital scales. For such embodiments, a tare button can optionally be provided.

The user then preferably presses on pad 18 and observes the resulting PFPR 33 on output display 11. A person applies downward, inward, squeeze or other pressure and force with finger, hand, palm, forearm, elbow or other body part or instrument to pad 18, thus generating an output by force sensors 23 and thus generating an output of PFPR 33 on output display 11. As different pressure and/or force is applied it can preferably be observed as a change of PFPR 33 on output display 11. Embodiments of touch trainer 100 can indicate the PFPR, through output display 11, visually and by sound, for example, by producing a sound or tone when the targeted PFPR is obtained, or illuminating an LED or other light when the PFPR is obtained. In another embodiment, touch trainer 100 is voice activated to set the PFPR and for general operating instructions, in which case touch trainer 100 preferably comprises a microphone 45 to receive audio input and comprises voice recognition software.

The user then preferably makes changes to the applied force exerted on pad 18, such as by adjusting the direction and/or effort of touch and observes how the resulting PFPR 33 is changed from its previous reading. The user then preferably continues to practice by applying pressure in different manners to pad 18 until the user is able to reproduce a target PFPR reading that was predetermined for a particular manipulation, modality or protocol. Proficiency is preferably attained when PFPR can be reproduced a predetermined number of consecutive times, which can optionally include five consecutive times.

Figure 3:
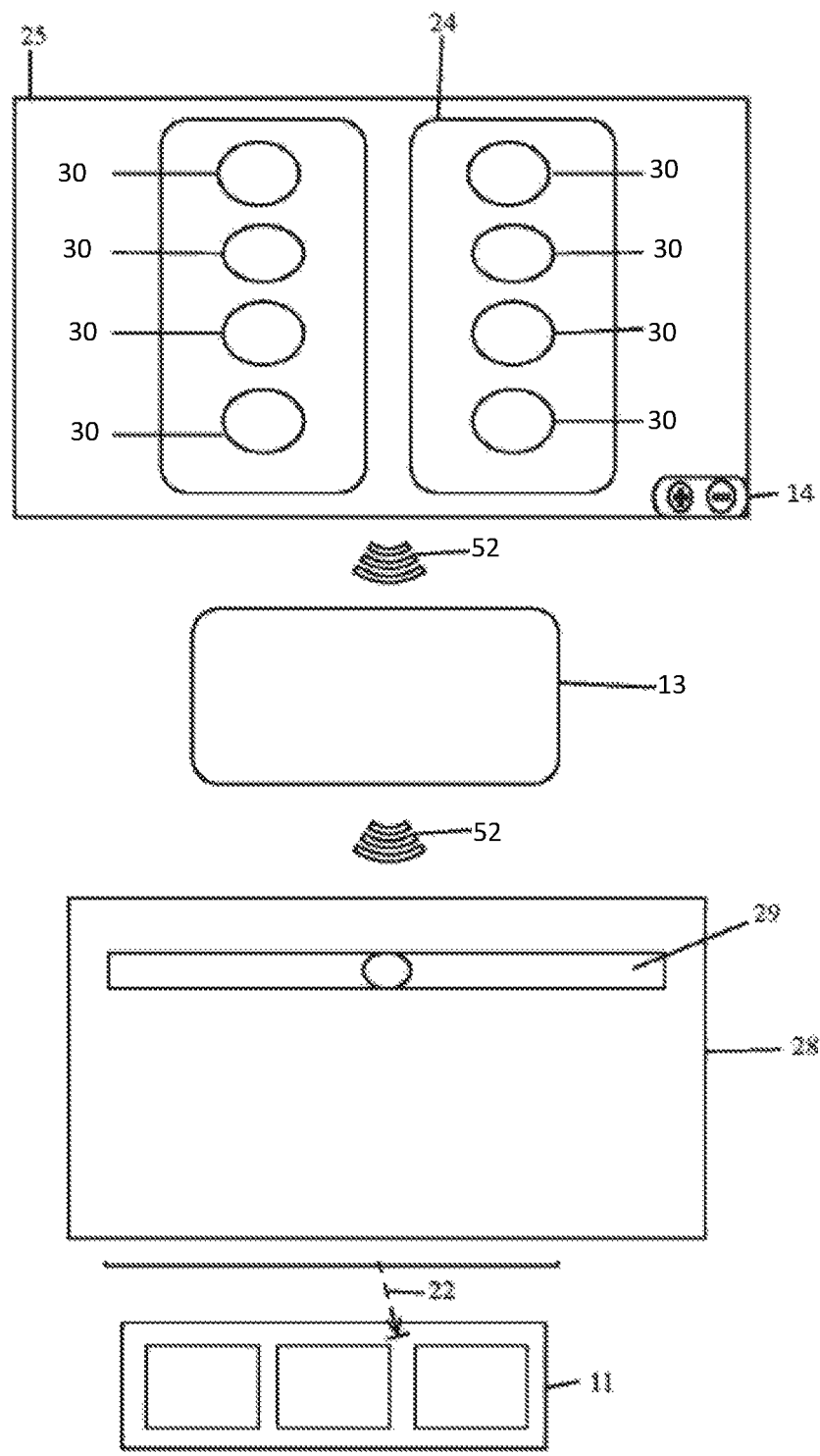
FIG. 3 is a drawing that illustrates biosensors in communication with a remote display according to an embodiment of the present invention.

FIG. 3 illustrates an embodiment where biosensors 30 are attached in sensor housing 24 that is embedded in a body connection apparatus 25. As used throughout the specification and claims, the term "biosensor" means any sensor that measures biological information, including but not limited to biometric and biofeedback sensors or actuators that detect a change in the circulatory, digestive, endocrine, integumentary, lymphatic, muscular or nervous system, and converts it into a signal which can then be measured or recorded, for example the sensors sold by Somatic Vision. Biosensors 30 monitor and record one or more of electrodermal activity or galvanic skin response, heart rate, heart rate variability, surface body temperature, respiration rate, carbon dioxide, pulse and oxygen, blood volume pulse, electromyography, electrocardiogram, air flow rate and capacity, segmental multi-frequency bioelectrical impedance analysis ("BIA") or bioimpedance spectroscopy ("BIS") to measure intra and extra cellular fluid, indocyanine green (ICG), and other sensors.

Figure 4:
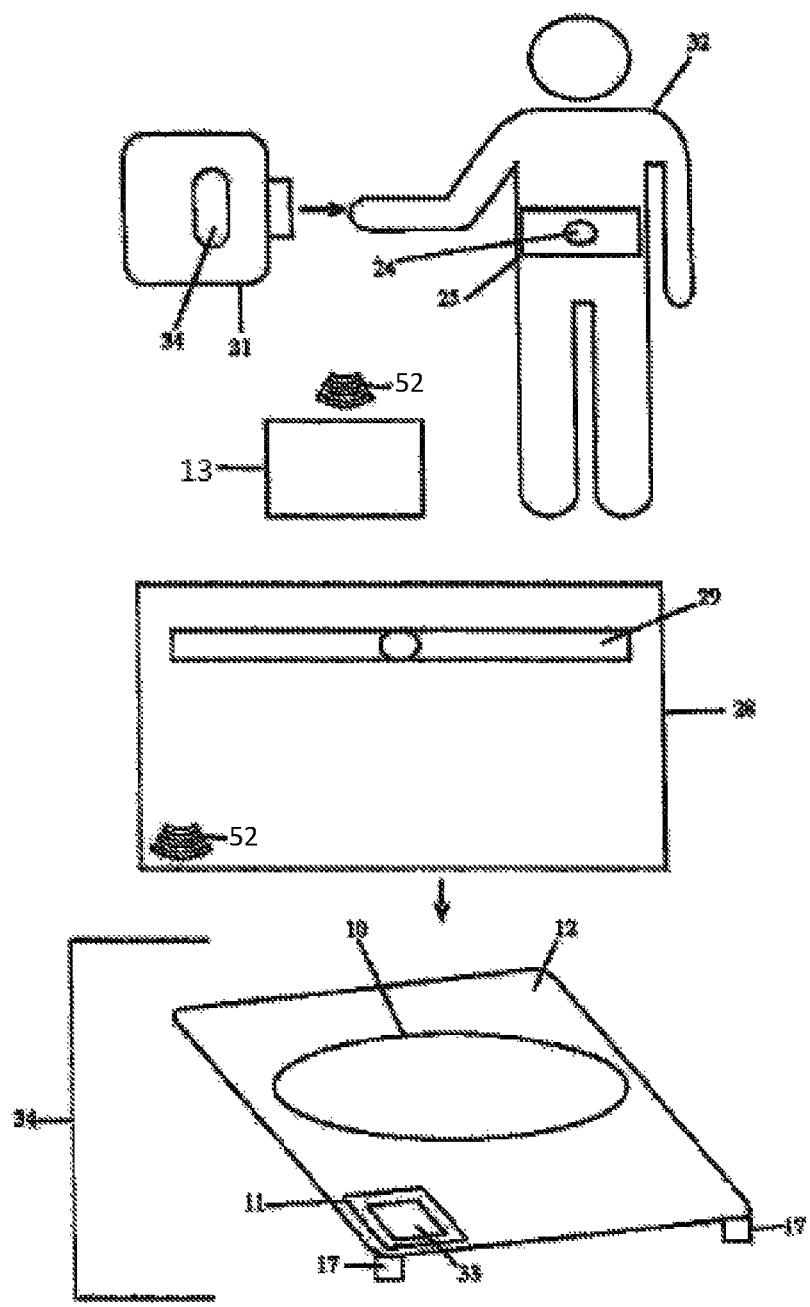
FIG. 4 is a drawing that illustrates how to measure the physiological effects of pressure and set protocol force pressure readings according to an embodiment of the present invention.

FIG. 4 illustrates algometer 31 applied to human 32. Sensor housing unit 24 that is embedded in body connection apparatus 25 is preferably connected to human 32. Sensor housing 24 preferably comprises a wireless 52 or wired data output to communicate data to processing unit 13. In one embodiment, remote display 28 preferably provides visual indication 29 in real time to illustrate the physiological effects of algometer 31. In one embodiment, algometer 31 is preferably pressed onto palpation area 10 where its force is detected by force sensor 23 and the resulting PFPR reading 33 of that pressure is displayed on output display 11.

By applying pressure to palpation area 10 and comparing the resulting output that is displayed on output display 11, therapists can adjust the amount of force exerted in an attempt to generate a desired PFPR. By continually making adjustments and practicing to obtain a desired PFPR, a therapist can thus train himself or herself to consistently generate a desired PFPR. By thus developing this skill, the therapist can thus consistently deliver a desired force pressure on a patient when performing a treatment. When such training and consistency is reproducible from one therapist to the next, the consistency of treatments can thus be improved. Once consistent treatments can be performed, results of treatments can be used to further improve treatment regimens.

The following describes how to create PFPR standards for manipulations, modalities and protocols that produce different physiological effects. In one embodiment, PFPR ranges can be assigned to modalities, including but not limited to Swedish massage, deep tissue massage, therapeutic massage, compression and others, as well as protocols created combining multiple modalities. Referring to FIG. 4, to create PFPR 33, one can use algometer 31 to define ranges based on sensation feedback or biosensor physiological data 26. Algometer 31 is preferably adjusted to a set pressure 34 which is then applied to a person. The user receives verbal feedback about the sensation from the person to which it was applied. Alternatively, or in conjunction with the verbal feedback, the user can observe and make interpretations based on biosensor physiological data 26.

In one embodiment, an instructor, organization, product developer, method creator, head therapist or other can use the intended modality or manipulation on touch trainer 100 and PFPR ranges can be set from the data on output display 11. In one embodiment, biosensors 30 that measure one or more of electrodermal activity or galvanic skin response, heart rate, heart rate variability, surface body temperature, respiration rate, carbon dioxide, pulse and oxygen, blood volume pulse, electromyography, electrocardiogram, air flow rate and capacity, segmental multi-frequency bioelectrical impedance analysis ("BIA") or bioimpedance spectroscopy ("BIS") to measure intra and extra cellular fluid, indocyanine green (ICG), and any other sensor that measures activity of the integumentary, muscular, skeletal, nervous, circulatory, lymphatic, respiratory, endocrine, urinary/excretory, reproductive or digestive system can also be used to create PFPR 33. The biosensors 30 can be attached to a person and an algometer 31 can be set to apply a controlled set pressure 34. The change in biosensor data 26 towards parasympathetic nervous system response can represent a reflexive effect and a change in biosensor data towards fluid exchanges in soft tissue can represent a mechanical change. The set pressure 34 applied by algometer 31 is preferably PFPR 33 for the manipulation, modality or protocol (as best illustrated at the lower portion of FIG. 4).

This same biosensor system can be used as an adjunctive tool for massage or diagnostic tool for manual therapists in treatment. Biosensors 30 can optionally be embedded into housing unit 24 that can be placed in cloth, neoprene, plastic or other fabric of connection apparatus 25 to be applied to a human or other animal. Biosensors 30 can connect with wires or wirelessly to transmit data 26 to processing unit 13 that preferably uploads data to software application 280. Of course, desirable results can also be obtained when processing unit 13 uploads data to a stand-alone computer or to a local area network. Remote display 28 that is connected to software application 280 can be placed in a treatment room and can thus transmit biosensor data 26 in real time. In one embodiment, biosensor data can be used to control an output that is observable to the user in real-time, including but not limited to adjusting the room environment in real time, thus providing visual clues to the therapist about the effects of the treatment.

Because consumers seek massage and manual therapy for both reflexive and mechanical effects, this biosensor system allows the manual therapy treatment to be adjusted using PFPR standards, in real time, to meet the consumers' goals in seeking treatment for reflexive or mechanical effects. The biosensor data can be communicated to the therapist in real time, thus allowing the massage/manual therapist to use the PFPR and adjust as necessary to produce the best therapy outcome. Embodiments of the present invention can also be used to set the first industry standards of reflexive and mechanical effects of manual therapies by defining PFPR that create the effects.

Referring again to FIG. 4 for an exemplary use of touch trainer 100 in a clinical setting, sensor housing unit 24 can be embedded into the body connection apparatus 25 and connected via a wire or wirelessly to transmit data 26 to processing unit 13. Remote display 28 can be disposed in the treatment room and can be connected to software application 280. The body connection apparatus 25 is preferably placed on the patient by hook and loop fastener around the fingers, toes or wrapped around the chest or other body part with a strap or other attachment mechanism. The therapist preferably confirms the system is operational by a visual indicator 29 on remote display 28. The therapist starts the treatment. As visual indicator 29 of the biosensor data starts to shift— including but not limited to heart rate decreases, body temperature decreases, etc., this is a reflexive PFPR 33 manipulation as these are body responses to parasympathetic nervous system response. As heart rate and body temperature increase, this is a mechanical PFPR 33 manipulation as these are body responses to increased fluid exchange at the soft tissue. A sliding bar on remote display 28 can provide the therapist a quick glance response at visual indicator 29 to easily see if the biosensor data is shifting to reflexive or mechanical effect of the manual therapy.

The combination of touch trainer 100 and its method and the real time reporting biosensor device (see FIG. 3) and its methods can be used for any manual manipulation, modality or protocol to remove subjectivity in training and treatments and increase the intended treatment outcome of the consumer. Touch trainer 100 and its methods of use can be used by other professionals, including but not limited to estheticians that apply pressure protocols to the face, in sports performance and training that applies pressures to the body to create effects and any other field of study that applies pressures to a body for an effect. For example, PFPRs 33 created through embodiments of the present invention can be taught to massage therapists. Therapists can gain proficiency in objective pressure delivery with the use of touch trainer 100 that provides pressure data feedback. Massage protocols, intended to deliver reflexive and mechanical responses, can be tested and verified with the biosensor device (see FIG. 3) and its method.

As illustrated in FIG. 6, pad 18 can be held in place via bezel 39 such that pad 18 can be attached to bezel 39 and another can be inserted. The term "bezel" can include any structure capable of holding pad 18. In one embodiment, bezel 39 does not comprise a large opening through which pad 18 is accessible, but rather, bezel 39 comprises a recessed area which accommodates pad 18.

Figure 8A:
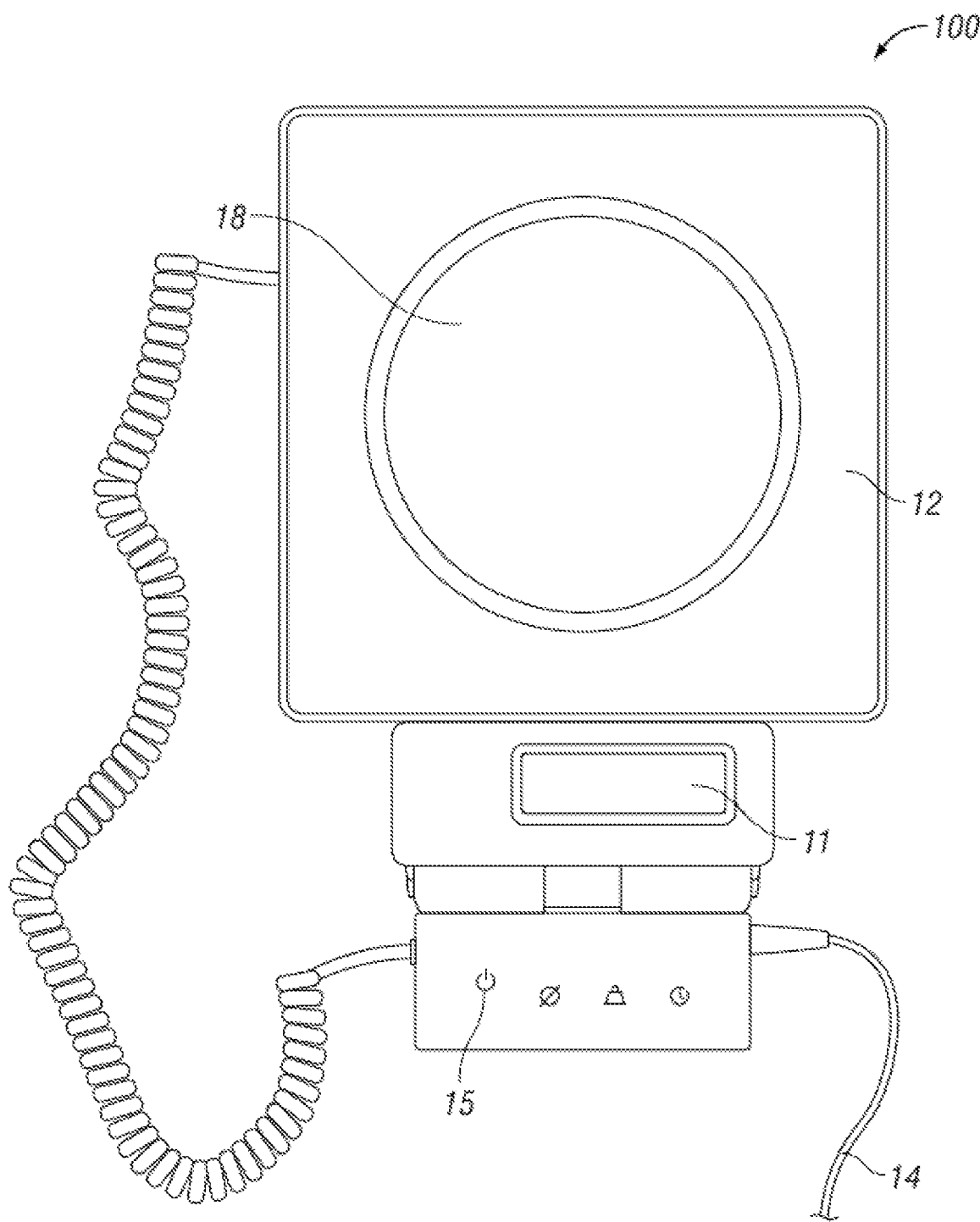
FIG. 8A is a drawing that illustrates a touch measurement apparatus according to an embodiment of the present invention with a pad disposed on a bezel that is attached to a top housing and which is connected to a wired output display.
Figure 8C:
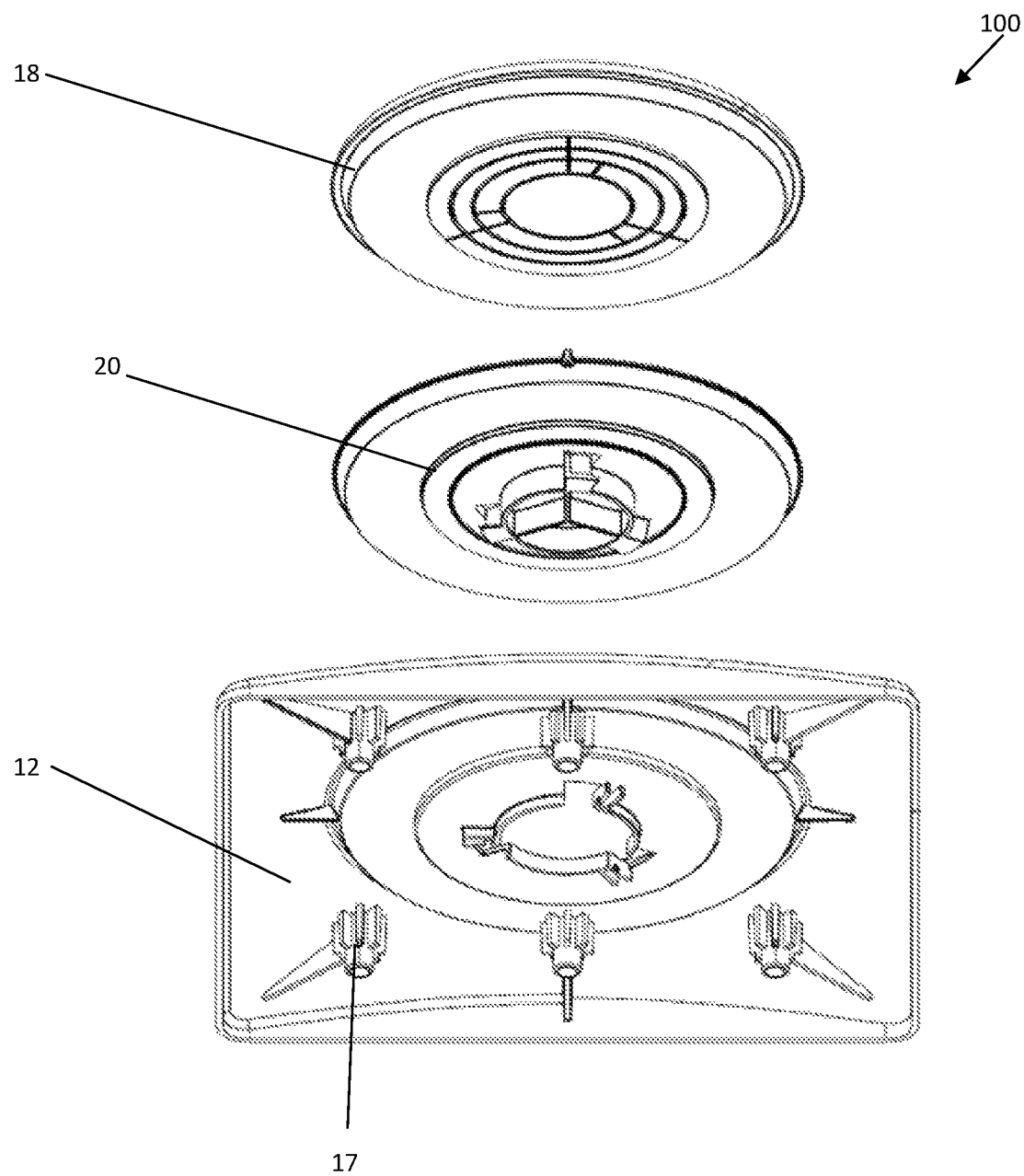
FIG. 8C is a drawing that illustrates an exploded perspective view from below of a touch measurement apparatus according to an embodiment of the present invention.

FIGS. 8A-8C illustrate various embodiments wherein bezel 39 is used in conjunction with a substrate 20 to support pad 18. Preferably substrate 20 comprises an overmold cup and latching device, which as best seen in FIGS. 8B and 8C, comprises projections that coordinate with base 12 to secure pad 18 at a certain orientation within base 12. As may be best seen in FIG. 21, substrate 20 may also have a latching tab 21 that projects out between base 12 and pad 18 that permits the user an object to grab to remove pad 18 out of base 12. Additionally, to lock substrate 20 (and hence pad 18) in place within base 12, substrate 20 can be shaped to coordinate with base 12 and/or comprise a locking device 520. In one embodiment, the recessed area of bezel 39 can itself comprise or can have attached thereto a securing apparatus or mechanism for securing pad 18 to bezel 39, for example, an adhesive, hook and loop tape, and/or mechanical fastener, including but not limited to a threaded rod can be disposed in the recess. In one embodiment, pad 18 is attachable directly to bezel 39 and bezel 39 translates force applied to pad 18 to substrate 20 and/or force sensor 23. In one embodiment, bezel 39 can function as substrate 20. Alternatively, bezel 39 can be removed from base 12 in order to replace one pad 18 for another. Preferably bezel 39 is made from a material that is both rigid and easy to manufacture into specific shapes, for example, bezel 39 is most preferably formed from Acrylonitrile Butadiene Styrene ("ABS"), High-density polyethylene ("HDPE"), Thermoplastic elastomers ("TPE") Thermoplastic Vulcanizate ("TPV"), Thermoplastic Polyurethene ("TPU"), Polyvinyl chloride ("PVC plastic"), Polyoxymethylene, stainless steel, steel, aluminum, combinations thereof, and the like. In one embodiment, air opening 40, or a plurality thereof, can be provided through bezel 39 and/or substrate 20. For embodiments wherein bezel 39 comprises a recess for disposing pad 18, air opening 40 is most preferably disposed in the recess. Air opening 40 permits pad 18 to be easily removed from bezel 39 and/or substrate 20 by permitting the entry of air to the bottom of pad 18 so that a suction-effect is not formed or sustained between pad 18 and bezel 39.

Pad 18 is preferably configured to simulate human tissue. For example, in one embodiment, pad 18 can be formed from thermoplastic, rubber, silicone, polyurethane, or another elastomeric material such as Dynaflex and Versaflex. In one embodiment, one or more items can be embedded into and form a portion of pad 18, including but not limited to: beads, marbles, or spheres, which can simulate the feel of knots and trigger points in a muscle; strips of rope, string, or twine, which can simulate the feel of structures such as tendons; cork to simulate scar tissue; and/or other materials to simulate the feel of subcutaneous features of living tissue.

By providing a quick replacement connection for pad 18, various simulated tissue structures can easily and quickly be interchanged to facilitate learning or training. In one embodiment, not only can the foregoing various materials be embedded in the pad material of different hardnesses, but the various materials can be imbedded at various depths within the pad so that different simulated tissues can be formed simply by changing the depth of the inclusion. In one embodiment, the inclusion can have a first material under it with a different material above it, thus forming pad 18 with a layered structure with an inclusion resting at an interfacing region of the two layers.

In one embodiment, pad 18 can be formed in a layered structure wherein two or more layers of pad 18 are formed from materials having different hardnesses with or without an inclusion. For example, in one embodiment, the bottom half or bottom fourth of pad 18 can be formed from a material having a first hardness while the remaining top half or top three-fourths can be formed from another material. Of course, this is merely one example and any number of combinations and layers of materials can be used to provide a pad formed from two or more layers of material having different properties.

While pads 18 can be provided in any desired material and any desired hardness to fit a particular application, in one embodiment, pads 18 are preferably provided in a range of Shore hardness to mimic subcutaneous tissues found in the body and changes that occur to those tissues with manual therapy application, including Shore hardness Shore A ranging from 0-100; Shore B ranging from 0-100; Shore C ranging from 0-100; Shore D ranging from 0-100; Shore 0 ranging from 0-100; Shore 00 ranging from 0-100; and other Shore hardness scales. In one embodiment, pad 18 preferably comprises a varying Shore hardness by providing elastomers in the same pad by layering the various materials—for example by layering the various hardness materials in a mold.

One or more procedures can be performed to pad 18 to mimic changes to subcutaneous tissues. For example, because urethane has a freezing point of −35° F., an ice pack can be embedded into a pad 18 formed of urethane and placed in a freezer. The freezer pack will freeze but the pad will not. In one embodiment, a user preferably places pad 18, with an ice pack disposed therein, in a freezer and lets it sit for a few hours or overnight. The user then removes pad 18 from the freezer and places it on base unit 12. As the user is providing manual therapy modalities to the pad, the freezer pack will begin to thaw (due to ambient room temperature and heat generated from manual manipulation) and will mimic the tissue hardness shift/change that occurs while performing manual therapy on living tissue.

Figure 5:
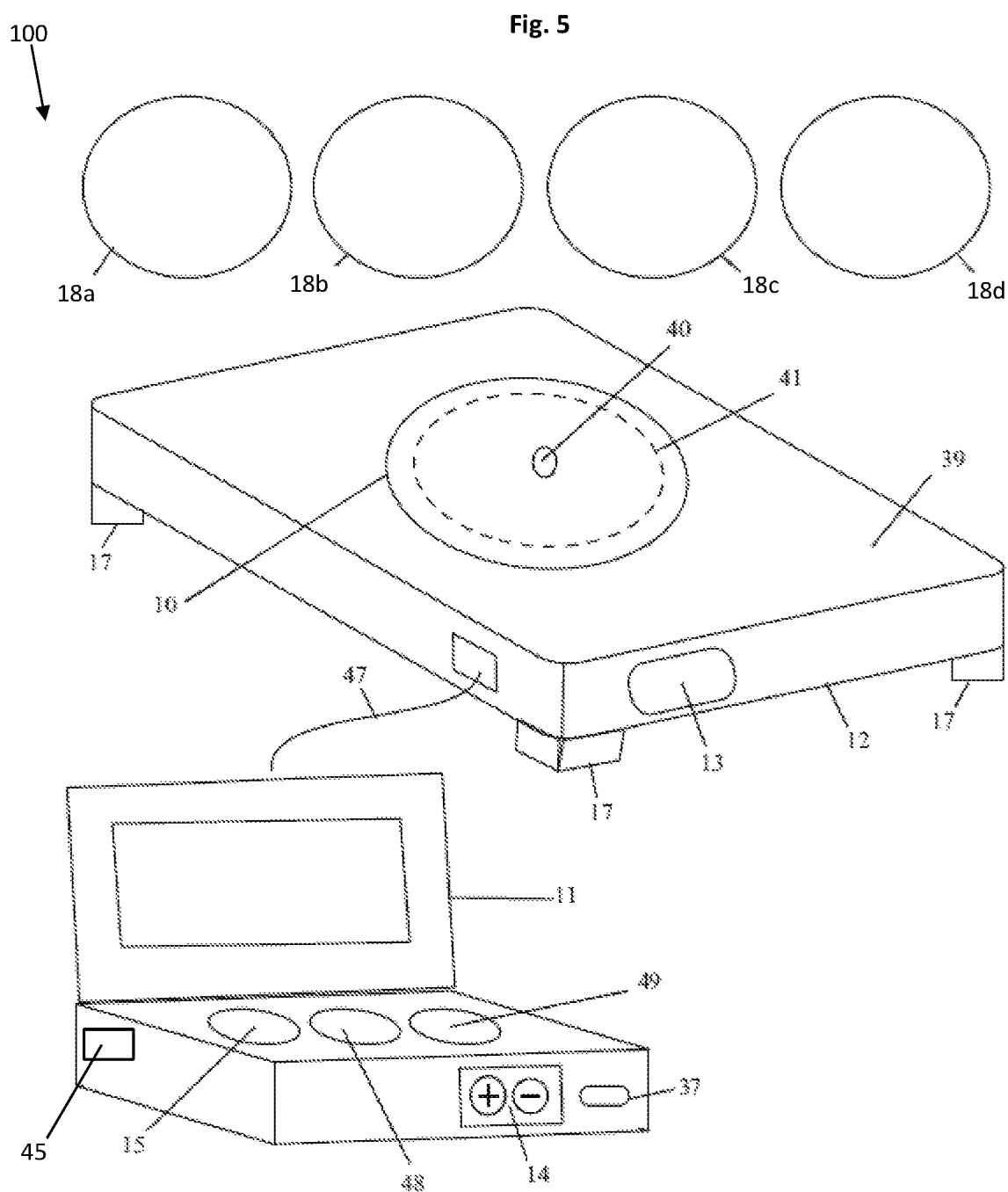
FIG. 5 is a drawing that illustrates a plurality of pads that can be interchanged on a touch measurement apparatus according to an embodiment of the present invention.

Pads 18 can be made into any shape including body parts, with any hardness and any material embedded in them to mimic subcutaneous tissues. As best illustrated in FIG. 5, a plurality of pads 18 having different material properties can easily be substituted for one another to provide a wide-range of simulated testing and/or training materials. A description of some exemplary pads and the simulated tissues that they represent follows. A first pad 18a is preferably provided as a representative universal pad having a Shore hardness of about 15 A with no varying layers or different structures disposed therein. This pad represents a regular tissue hardness and is easy to use in training. A second pad 18b can be formed from a material having a Shore hardness of about 40

A without intervening layers or imbedded material. This pad mimics fibrous tissue like those present in lymphedema or dense muscles such as that of athletes as well as hypertonic tissue found with central nervous system injuries as well as others. A third pad 18c is preferably provided which simulates a delicate material and can have a Shore hardness of about 10 A. This pad preferably has a thickness of about ½ that of the foregoing pads such that it mimics facial tissue/skin as well as the tissue of babies and geriatrics. A fourth pad 18d is preferably provided having a Shore hardness of about 10 A. In this pad, a freezer pack is preferably embedded therein such that it is surrounded with a material having a Shore hardness of about 10 A. This pad mimics tissue hardness change due to manual therapy manipulation. Of course, the freezer pack can be imbedded in any of various other materials having different Shore hardness. A fifth pad (not shown) is preferably provided which mimics bone material. In this embodiment, the pad is preferably formed from a material having a Shore hardness of about 60D or greater, which mimics bones and vertebrae. A sixth pad (not shown) is preferably provided which mimics adipose tissue. In this embodiment, the pad is preferably formed from a material having a Shore hardness of about 5 A. A seventh pad (not shown) is preferably provided which mimics teeth. In this embodiment, the pad is preferably formed from a material having a Shore hardness of about 100 or greater, which mimics a human mouth.

The foregoing examples are meant to merely illustrate one possible grouping of pads 18 that can be provided and that can easily be interchanged with one another on touch trainer 100. Touch trainer 100 is preferably capable to report, through output display 11 or otherwise, force sensors 23 within pads 18 both individually and/or as a group.

As further illustrated in FIG. 5, air gap 40 is preferably disposed through base 12 and, if used, through substrate 20 (see FIG. 2). Optionally, an adhesive 41 material or connection mechanism 41 can be used to secure pad 18 to base 12. For embodiments wherein base 12 is intended to be placed on a horizontal surface, feet 17 are most preferably provided. Although processing unit 13 is most preferably disposed in or on base 12, in one embodiment, it can be external to base 12. One or more output displays 11 can be separated a distance from base 12, via connection 47, which can optionally be wired or wireless and which an optionally include not only data connection to output display 11, but which can also optionally include power to output display 11. A units selection input 48, which can for example optionally switch between standard or metric units and/or between pounds and/or ounces is preferably provided. A calibrate, a.k.a. "tare" input 49 can also be provided to clear and/or zero the unit—particularly when switching between various types of pads 18. On/off switch 15 is also optionally provided. In one embodiment, connection 37 can be provided for universal serial bus ("USB") and/or a wired or wireless connection—particularly for using the invention in conjunction with a web or non-web based application. Although FIG. 5 illustrates these various inputs and connections as residing on output display 11, it is to be understood that these items can be placed anywhere on the invention and desirable results will still be obtained.

Touch trainer 100, by adapting pad 18, can be used by and/or in the training of a diverse range of professionals, including but not limited to: Massage Therapists, Occupational Therapists, Physical Therapists, Chiropractors, Acupuncturists, Certified Athletic Trainers, Personal Trainers, Estheticians, Veterinarians, Veterinary Assistants, Nail Technicians, Dentists, Dental Hygienists, Sports Medicine, and any other profession that uses manual manipulation or uses tools that apply pressure or pressure application to the body or to another surface. Products and tools that are used on the body can be used on pad 18. For example, microneedling and other facial application tools can be trained and standardized on pad 18—particularly when pad 18 is formed from a delicate material, such as the third pad in the preceding list of exemplary pads. Products that encourage fluid exchange can be applied or wrapped around pad 18—particularly when pad 18 is shaped as an anatomical part; for example, a human leg. Tattoo artists can practice on pad 18 to learn about line blow out pressure. Chiropractors can use activators on pad 18 to practice applying pressure to one or more anatomical features of a patient, such as a patient's spine. For applications wherein touch trainer 100 is used to evaluate and/or train persons with regard to the application of force to inanimate objects, pad 18 is preferably provided via a material that simulates the inanimate object on which the user will work, and the base preferably is of a shape that simulates the object or activity as well. For example, when touch trainer 100 is used to train, test, and/or evaluate a baker in the amount of force in kneading dough, pad 18 is most preferably formed from dough or a material that simulates the dough. For applications wherein a sculptor is simulating the amount of force to strike a small chisel against marble, pad 18 is preferably formed from marble or a material that simulates marble. Base 12 of touch trainer 100 can also be adapted for any particular use. For example, touch trainer 100 can be placed on a horizontal surface, and in another embodiment, touch trainer 100 and/or any components thereof can be installed on a wall or another vertical or non-horizontal surface and/or incorporated into a body pack.

Embodiments of pad 18 can comprise tubes embedded within pad 18 to create the effect of physical characteristics like veins, arteries, ligaments, etc. and can provide liquid flowing through the tubes. Another embodiment of pad 18 does not comprise tubes. In one embodiment, the pressure of a simulated massage is measured with an apparatus according to an embodiment of the present invention when a massage to a person or other living animal is not actually being performed. In one embodiment, the apparatus of the present invention records force readings that are not contemporaneous or otherwise concurrent with an actual massage being performed, for example, an embodiment of the present invention provides force measurements when a living subject is not being subjected to a massage or other treatment. In one embodiment, when a massage or other physical manipulation is being performed to a human or animal, the thing exerting the force on the human or animal is a human and is not a robot or a remote manipulator.

In one embodiment, a PFPR can be formed by initiating a PFPR testing protocol to confirm a user's proficiency comprising the steps of: turning on touch trainer 100; assigning a pad 18 to a trainee, which can optionally be assigned by associating the trainee's name with the RFID chip in pad 18; trainee inserting pad 18 into touch trainer 100 and, if necessary, zeroing out the unit; instructor placing a monitor out of the line of sight of trainee; instructor instructs trainee to apply a protocol force pressure within a predetermined range; after a predetermined amount of time, the trainee ceases to apply the force, optionally at the instructor's instruction; repeating the foregoing steps as instructor desires or preferably according to a standard, for example, if the trainee correctly applies a force within the requested range a predetermined number of times—for example all five times—the trainee can be deemed proficient in that standard; repeating the foregoing with each trainee.

Touch trainer 100 can be used in non-PFPR applications. For example, touch trainer 100 can be used as part of an applicant screening process for educational, training programs and/or employment. Touch trainer 100 can also be used once or more before, during, and/or after a shift to measure and/or track therapist shift fatigue to reduce injury and improve the quality of service delivery.

An embodiment of the present invention provides a line of communication not currently present for non-verbal and hearing impaired clients/patients/consumers. In this embodiment, biosensor data can be sent to a remote display or integrated to control the environment of the treatment room by creating a change in lighting color/richness, room temperature, music volume/selection and others. For example, a therapist may provide a massage that he or she intends to produce a reflexive effect or relaxation. As the biosensor data is collected from the patient, and a change in nervous system response is detected, the lights in the treatment room can be made to dim and/or change color to produce a visual response to the therapist that the technique is producing the intended effect. This can be repeated with room temperature, table temperature, aromatherapy, music volume and/or selection and others. This same concept can apply to anyone with wearable technology such as Fitbit® and a smart home hub such as Phillips Hue®. An embodiment provides an apparatus and method that bridges the biosensor wearable technology and smart home integration into a hub.

An embodiment of the present invention also provides a personal biosensor data device that can control home/work/treatment room environments including temperature, lighting, music and others. The data collected on a wearable device can be integrated with devices of a "smart home". For example, if a consumer needs to get better sleep, the consumer can be fitted with a wearable device that provides important sleep data and the consumer can program all types of devices to do a certain function when the consumer wants to wake up, retire to sleep, etc. But, no current device controls these things based on the actual physiological data from the person and the programmed information. As the consumer is sleeping, ambient room temperature can be adjusted, and white noise, aromatherapy, and lighting can be controlled to maximize REM sleep cycle. When it is the scheduled time to wake up, the systems are preferably controlled by the data to provide the most efficient environment for the intended goal.

Optionally, products, including but not limited to creams, gels, lotions, oils, braces, compression garments, and others can be tested in conjunction with an embodiment of the present invention to measure their reflexive and/or mechanical effect response to treatment. In this embodiment, such items can be used in conjunction with touch trainer 100—particularly when combined with a biosensor system to create product application standards that are evidence-based.

An embodiment of the present invention can be used to standardize how the reflexive and mechanical effects of manual therapy, product application, etc., are woven through processes of the industry. This is preferably accomplished by any of the following: defining a consumer treatment goal or screening process, as described further below; matching a proficient therapist under PFPR Testing PROTOCOL and confirming therapist proficiency; delivering set PFPR in treatment, for example as described previously in this application; monitoring consumer biosensor physiological data in real time; and recommending proven products and treatment frequency to increase outcomes.

An example of a client/consumer/patient screening process includes accurately screening consumers to uncover their goals in seeking treatment, reflexive, mechanical or both and appropriately matching their treatment goals with services and a therapist that has been verified as proficient in the intended effect. This decreases therapist intake time, increases treatment outcomes, consumer satisfaction and therapist job satisfaction. It also increases quality and service standards.

Subjective, objective, assessment and plan ("SOAP") charting is preferably accomplished using objective PFPR by creating objective treatment notes by documenting the reflexive and/or mechanical effects produced by delivering the defined PFPR. This allows evidence-based treatment outcomes to be documented over time to increase treatment outcomes, customer satisfaction and retention while meeting the legal charting mandate. This also allows non-verbal people and hearing impaired to communicate treatment goals and results. It also permits one to develop and test treatment frequency with real data that can be tracked over time and to develop and test products for frequency and application rate.

Figure 7:
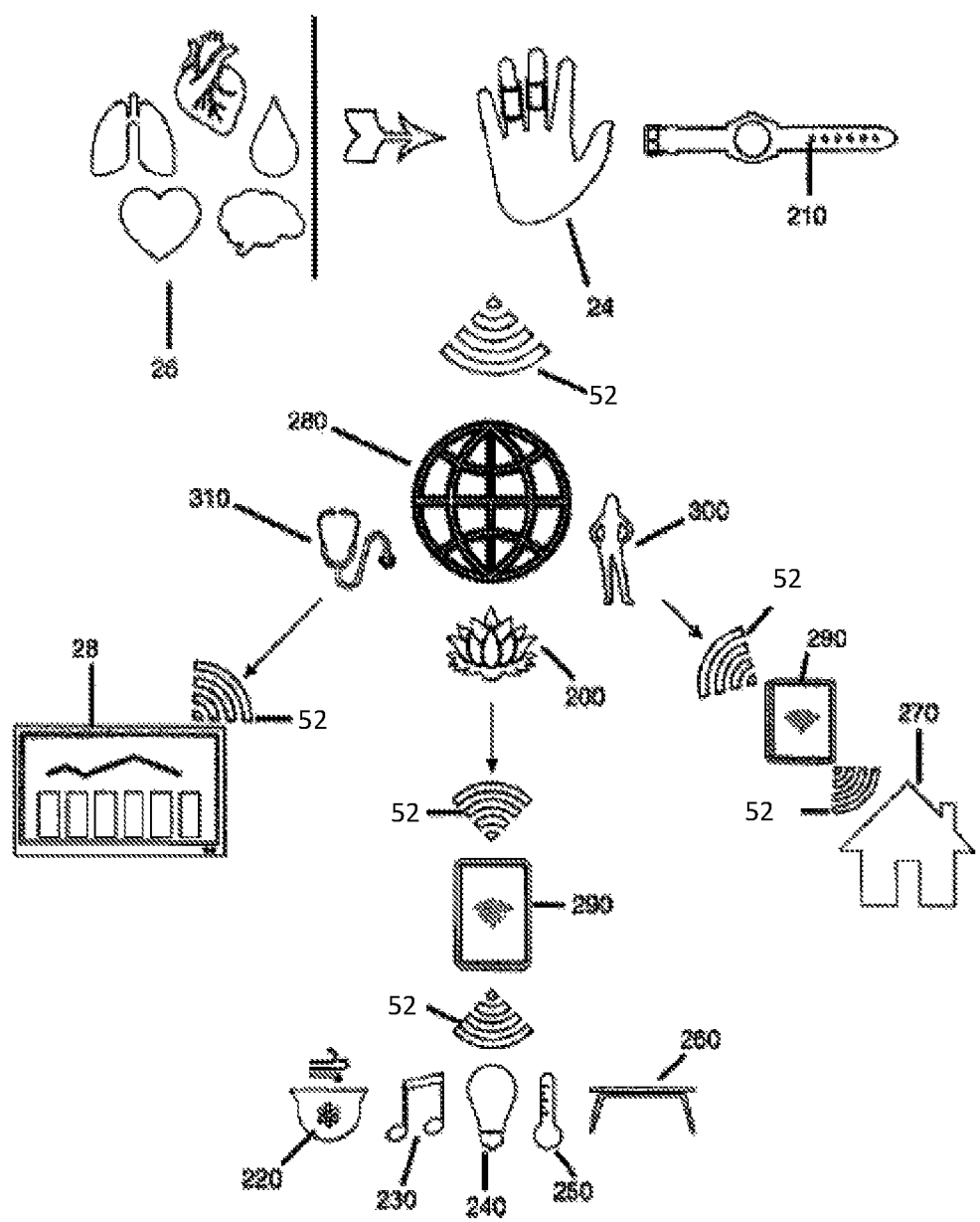
FIG. 7 is a drawing that illustrates a process of biosensor data integration according to an embodiment of the present invention.

Referring now to FIG. 7, an embodiment of the present invention can provide desirable results when used in a treatment room environment of spa 200, which can include other types of wellness centers or spa environments. Clinical environment 310 can also provide benefits from using embodiments of the present invention. Home and/or office environments 300 can also provide benefits from using embodiments of the present invention. In one embodiment, a consumer's biosensor data 26 can be collected, most preferably in real-time or near real-time, from biosensors 30 disposed in sensor housing 24. Data 26 is the preferably transmitted from wearable technology 210 to a software application 280. Software application is preferably web-based or app-based. Integration hub 290 can be a network-connected integration point for software application 280 and the network-connected devices. As the consumer data shows a shift towards reflexive or mechanical effects, that data directly controls the network-connected devices, thus creating a unique, personalized and effective treatment room environment.

Lighting 240 can optionally become dimmer, softer, brighter or a different color to provide visual clues for the therapist to confirm a shift towards reflexive or mechanical effects of treatment. Room temperature 250 can increase or decrease based on peripheral skin temperature measurement, or to encourage fluid exchange and a greater shift towards mechanical effects. Music and sound level 230 can be adjusted such that the invention automatically controls the music selection and/or sound level to produce a greater mechanical and reflexive effect shift. Treatment table temperature 260 can be increased or decreased based on peripheral skin temperature measurement to produce a greater mechanical and reflexive effect shift. Aromatherapy 220 can be adjusted such that the invention automatically selects and controls the saturation of essential oil to produce a greater mechanical and reflexive effect shift through scent. In one embodiment, wearable technology 210 can transmit data 26 to a smart home system, or networked connected devices, including but not limited to lighting, thermostat, music and others. Program settings can be pre-loaded and can optionally include sounds for sleep, wake, energy, focus, relaxation, exercise and others. Biosensor data can be collected in real time, and processed through the selected program setting before adjusting network controlled devices in a home or office based on biosensor data to provide the most efficient and immersive environment to achieve health goals.

Touch trainer 100 can be used to establish a certification program to ensure that a person can transfer a desired amount of force to pad 18 within a specified range. For example, in one exemplary embodiment, a certification program can require that a professional Standard Touch Practitioner provide: 6 continuing education units ("CEU's"), proficient in Product Application 2-5 LB delivery; and proficient in Swedish Massage 10-20 LB delivery. A certification program can require that an expert Standard Touch Practitioner: must be a Professional Standard Touch Practitioner; complete 10 CEU's; be proficient in therapeutic massage 25-35 LB delivery; and be proficient in deep tissue massage 35-50 LB delivery. A certification program can require that a Clinical Standard Touch Practitioner: must be an Expert Standard Touch Practitioner; complete 10 CEU's; and be proficient in ischemic compression 50-80 LB delivery. A certification program can require that a Standard Touch Certified Business have a percentage of clinical staff that must be Standard Touch Certified. A certification program can require that a Standard Touch College, School, and/or University must teach using objective touch standards. A certification program can require that a Standard Touch Instructor must be able to teach techniques, modalities and protocols on standard touch, and provide Standard Touch Practitioner certification.

In another exemplary certification scheme, a Mendology™ certified business can be required to complete all trainings, including wellness service applicant screening process, SOAP plus, front desk consumer screening process, meet consumer treatment goals so products sell themselves, protocol standardization for customer retention, measure/track therapist shift fatigue to reduce injury, and confirm therapist proficiency. A Mendology™ Master Trainer can be required to: set protocol ranges training; perform quality and service standards training; perform reflexive and mechanical response to touch; use the standard touch; and have touch proficiency.

Figure 9:
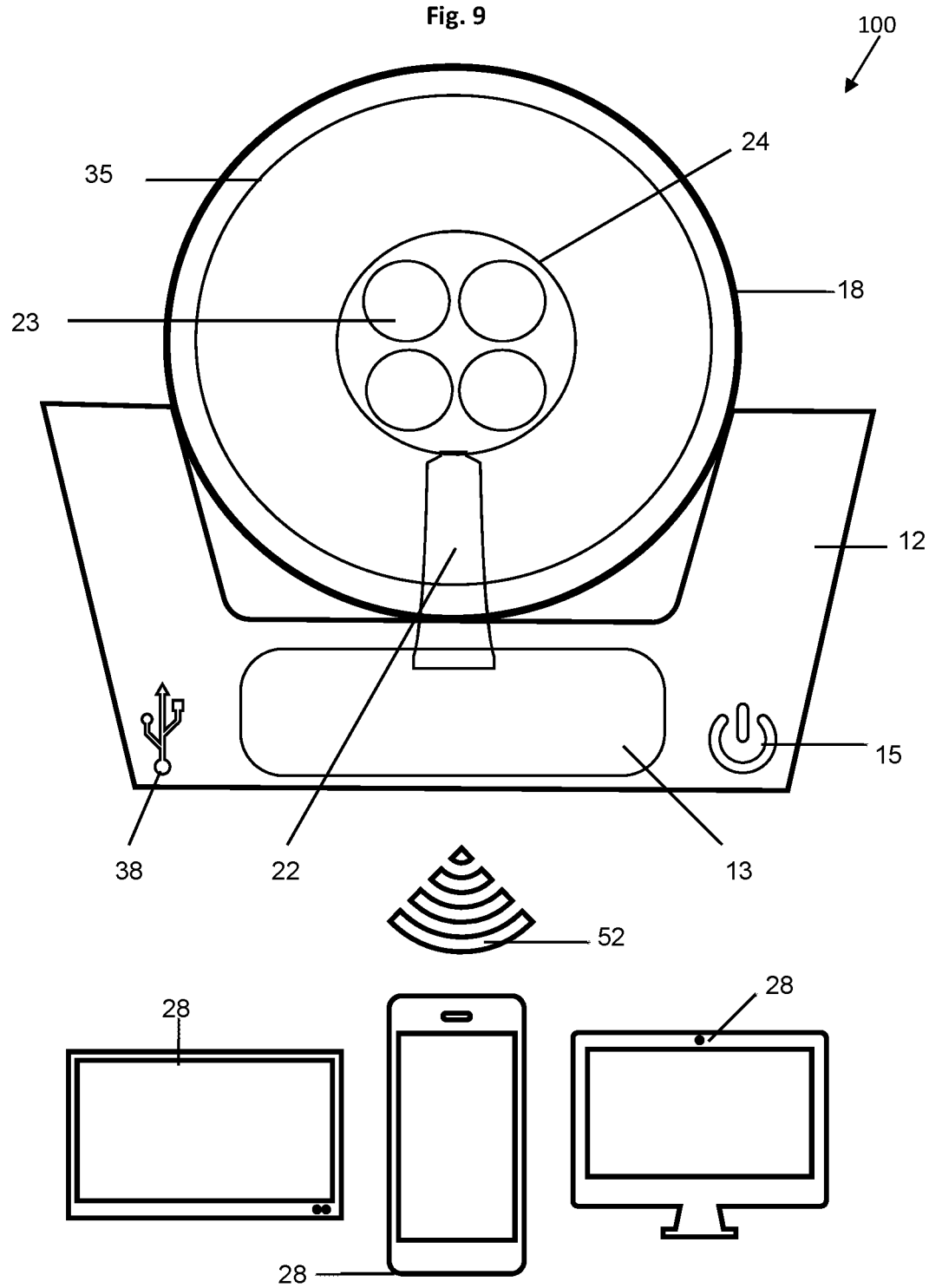
FIG. 9 is a drawing that illustrates a touch measurement apparatus according to an embodiment of the present invention with multiple measurement sensors embedded in a 3D sphere palpation pad and which communicates with a remote display through a web-based or app-based application.

Referring to FIG. 9, touch trainer 100 can comprise a 3D pad 18 comprising multiple force sensors 23. Preferably, pad 18 is a sphere to allow for varying planes for different manual techniques and manipulations that require any combination of squeeze, pressure, acceleration, torque, torsion, velocity, mass, force, friction, kinetic energy, tilt and position. Sensor housing 24 holds force sensors 23, which preferably monitor and record pressure, acceleration, torque, torsion, velocity, mass, force, friction, kinetic energy, tilt and position, and not physiological measuring sensors. To monitor if the user's whole hand is in contact with pad 18 or just the user's finger etc., pad 18 preferably comprises pressure-sensitive conductive sheet 35, such as Piezo film or filament.

Figure 10:
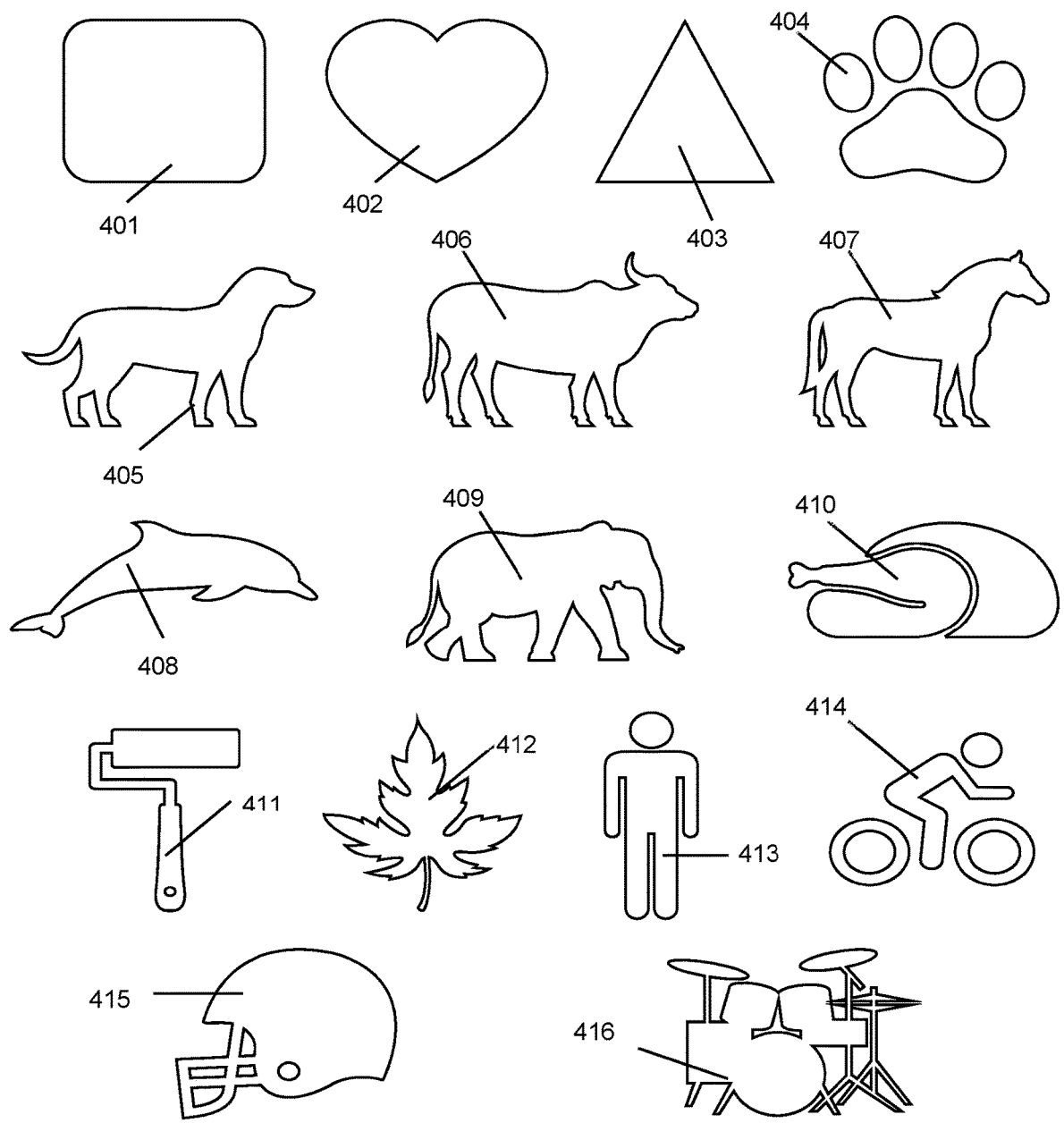
FIG. 10 is a drawing that illustrates a plurality of shapes for the palpation pad according to embodiments of the present invention.

Referring to FIG. 10, pad 18 can take various shapes in the various embodiments of touch trainer 100, including but not limited to: square 401; heart 402 or other anatomical shape; triangle 403; paw print 404 or other small animal anatomical shape; dog 405 or other small animal; cow 406 or other livestock animal; horse 407 or other equestrian related shape; dolphin 408 or other marine life related shape; elephant 409 or other wild animal related shape; culinary 410 or other food related shape; trade tool 411 or other construction, art and/or craft shape; leaf 412 or other nature shape; body 413 or other mammal shape; cycle 414 or other related sport transportation shape, for example, motocross bike, BMX bike, jet ski, snow mobile, etc.; football helmet 415 or other sport related shape; and drum set 416 or other musical instruments.

Figure 11:
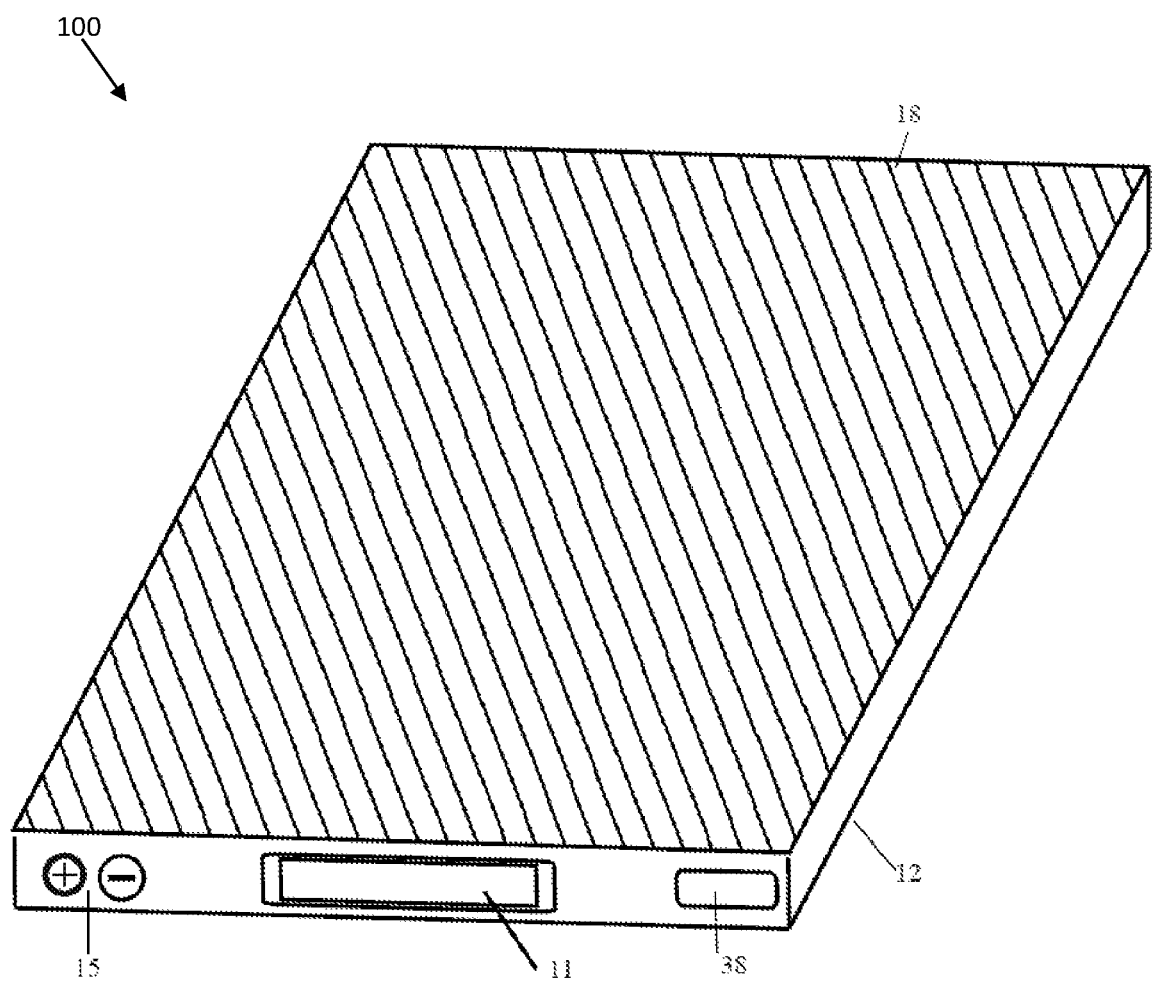
FIG. 11 is a drawing that illustrates a touch measurement apparatus according to an embodiment of the present invention with a palpation pad comprising multiple sensors, and in which all electronics are in the base housing and which communicates to a remote display by wifi, bluetooth and/or a web-based and/or cloud-based application.

In some embodiments of touch trainer 100, pad 18 is not removeable, that is, the pad is integrally manufactured as a unit with touch trainer 100, for example as illustrated in FIG. 11.

Figure 12:
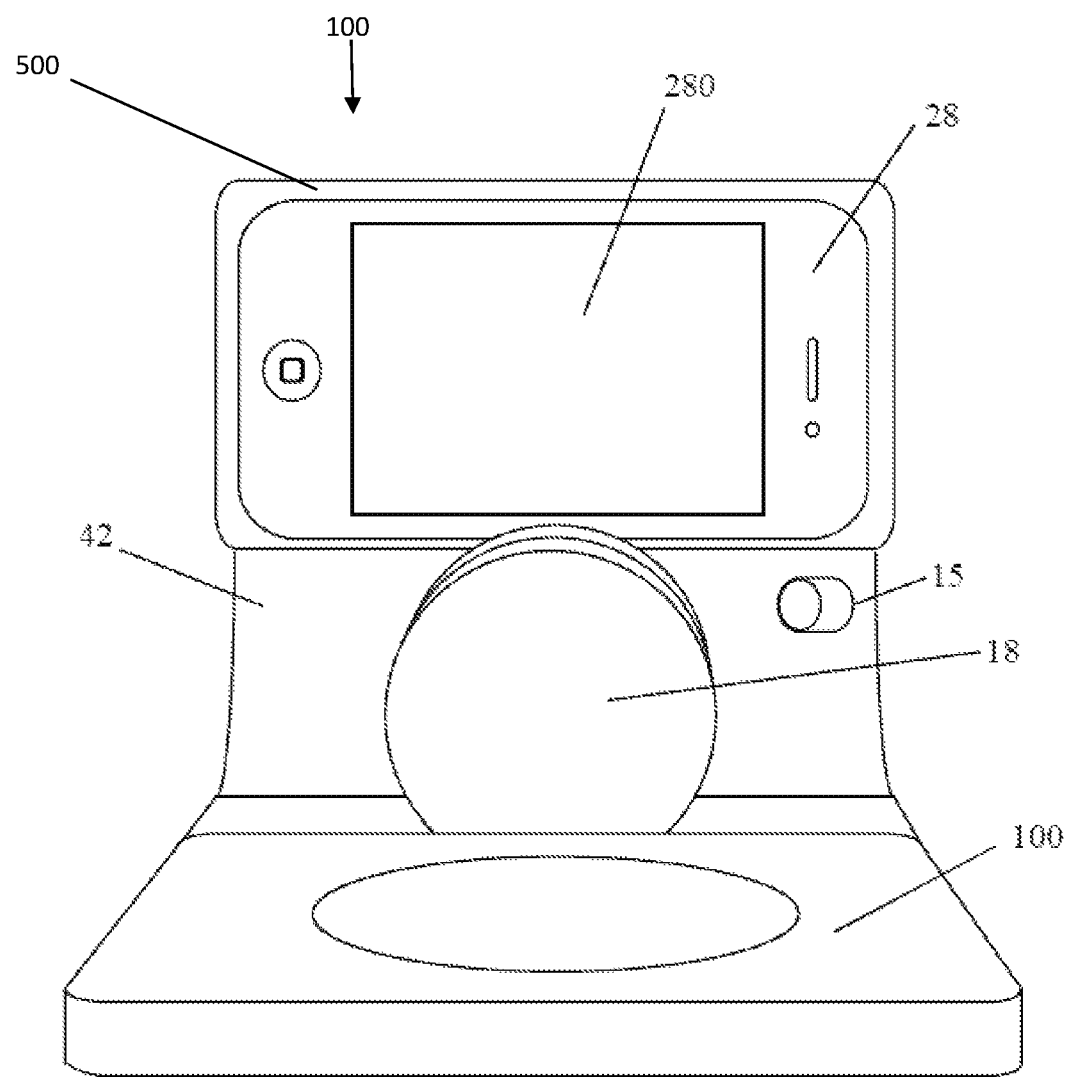
FIG. 12 is a drawing that illustrates a touch measurement apparatus according to an embodiment of the present invention with a palpation pad fixed to the housing unit with an on-board display.

Referring to FIG. 12, embodiments of touch trainer 100 can also comprise accessory stand 500. Preferably, accessory stand 500 mounts a mobile device such as a smart phone or tablet above touch trainer 100 and organizes/stores palpation pads 18.

Figure 13:
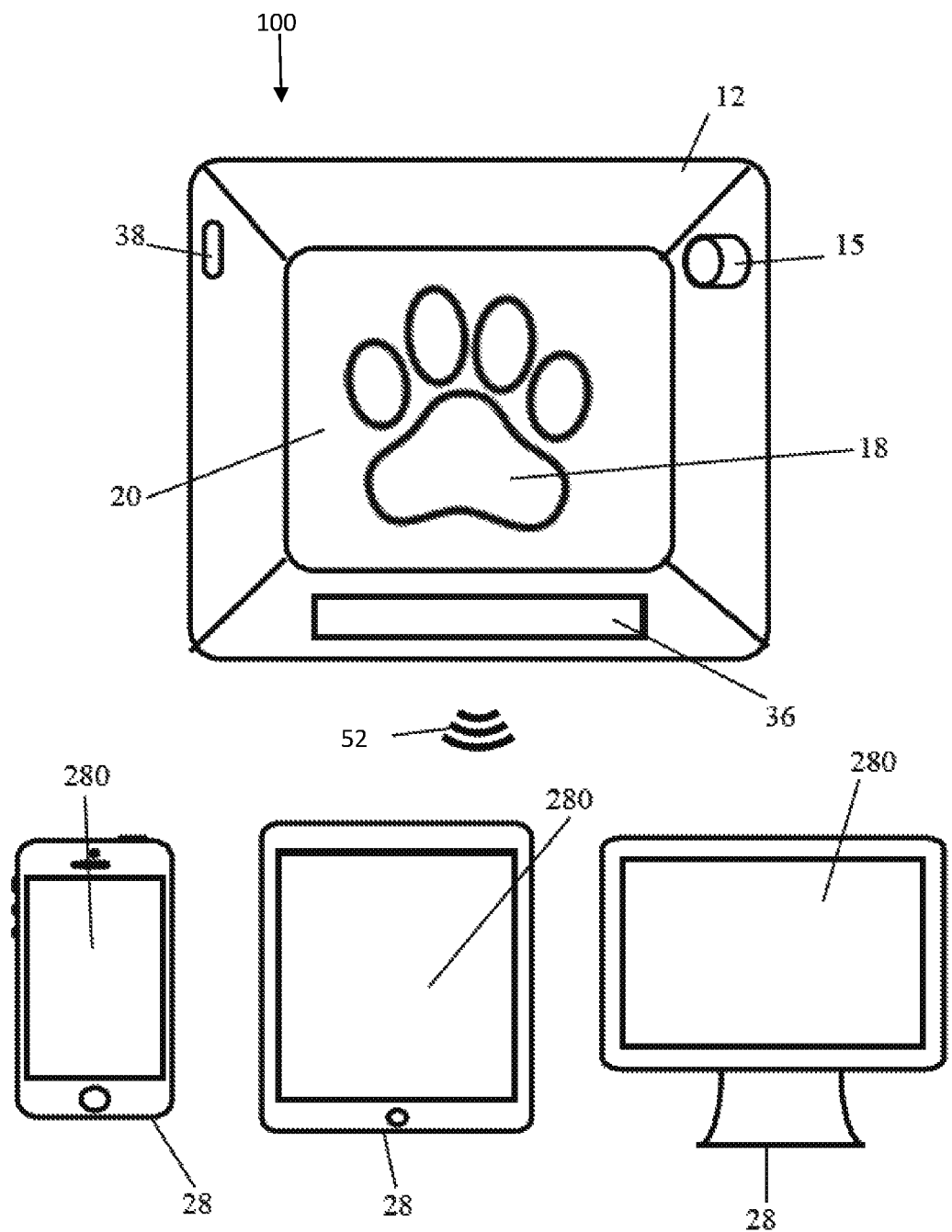
FIG. 13 is a drawing that illustrates a touch measurement apparatus according to an embodiment of the present invention with a palpation pad fixed to the housing unit with an on-board display used for pet owners.

Touch trainer 100 can also be adapted for use by pet owners, for example, to ease the discomfort of an aging pet by teaching pet owners techniques and pressures to apply to a pet, and to teach pet owners the correct pressure to be used to maximize the success of training a pet. Referring to an embodiment of touch trainer 100 illustrated in FIG. 13, pet owners can learn how to provide touch therapy to their animals through an interactive software application 280 connected to touch trainer 100. Touch trainer 100 can also be adapted to train livestock owners how to, for example, massage a cow in the Kobe beef tradition, or to massage livestock to enhance their mobility or address other physical issues.

Figure 14:
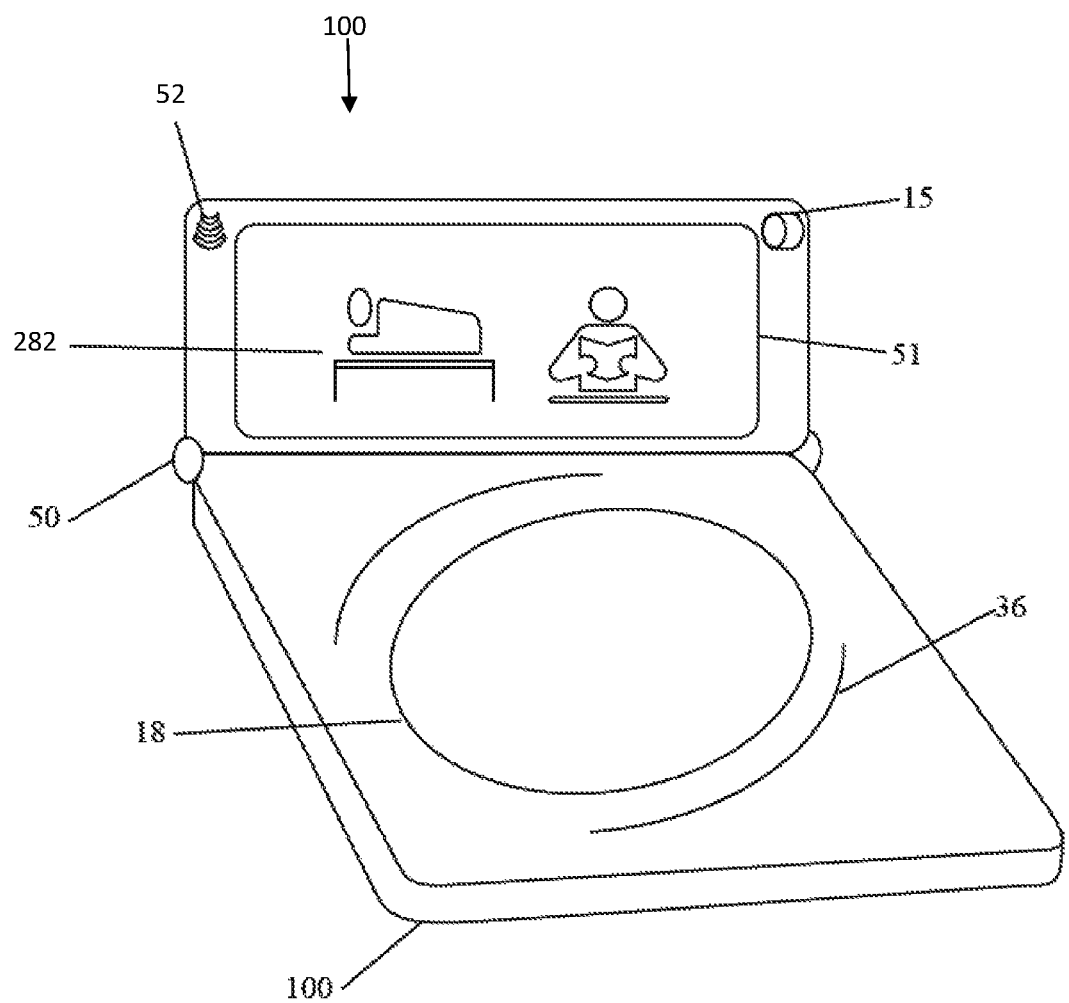
FIG. 14 is a drawing that illustrates a touch measurement apparatus according to an embodiment of the present invention with an onboard LCD display, that connects to the internet and that has embedded web-based, app-based or preloaded training programs including videos and testing protocols.

Referring to FIG. 14, embodiments of touch trainer 100 can comprise an onboard LCD screen 51. Preferably, touch trainer 100 connects to internet and has embedded web-based or app-based or preloaded training program 282, including videos and testing protocols, that displays through onboard LCD screen 51. LCD screen 51 can essentially take the place of a smart phone/tablet etc. Preferably, swivel 50 allows the user to adjust the angle of LCD screen 51 in relation to touch trainer 100. Indicator light 36 can illuminate to confirm if the manipulation or technique performed by the user was performed correctly or incorrectly.

Figure 15:
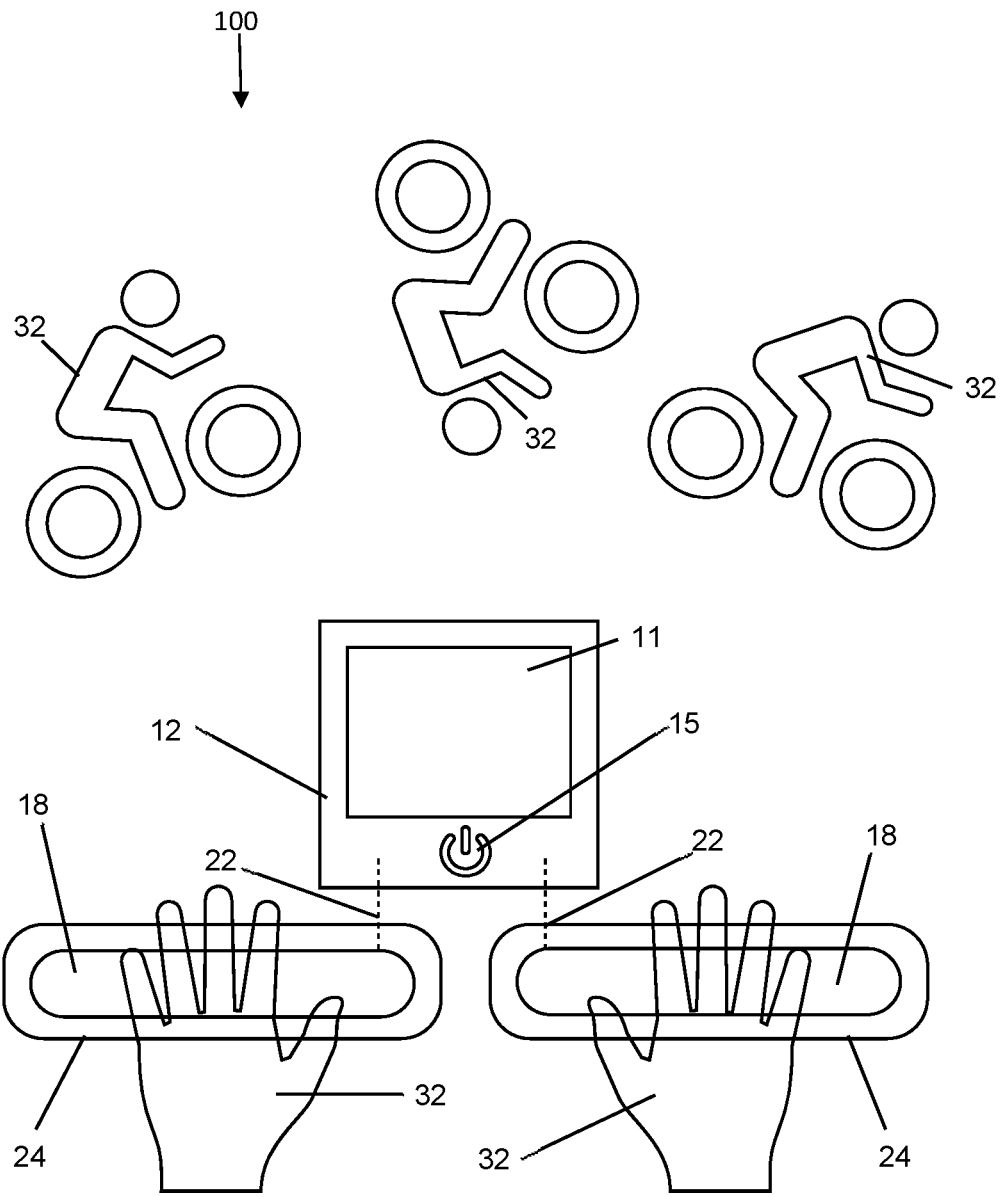
FIG. 15 is a drawing that illustrates a touch measurement apparatus according to an embodiment of the present invention used for extreme sports comprising simulator handle bars used to train a person to complete a 360 degree turn on a bike before the person practices on the bike.

Referring to FIG. 15, touch trainer 100 can be adapted for use to train for extreme sports. The body mechanics used in successfully completing a 360 trick can be trained before practicing on a bicycle. In the case of adapting touch trainer 100 for training for the use of a bike, sensor housing 24, or additionally or alternatively the pad 18, preferably takes the form of handle bars around which the user's hands 32 can wrap, that is, two separate housings of an elongated cylindrical or rectangular shape connected to base 12 through electrical connections 22.

Figure 16:
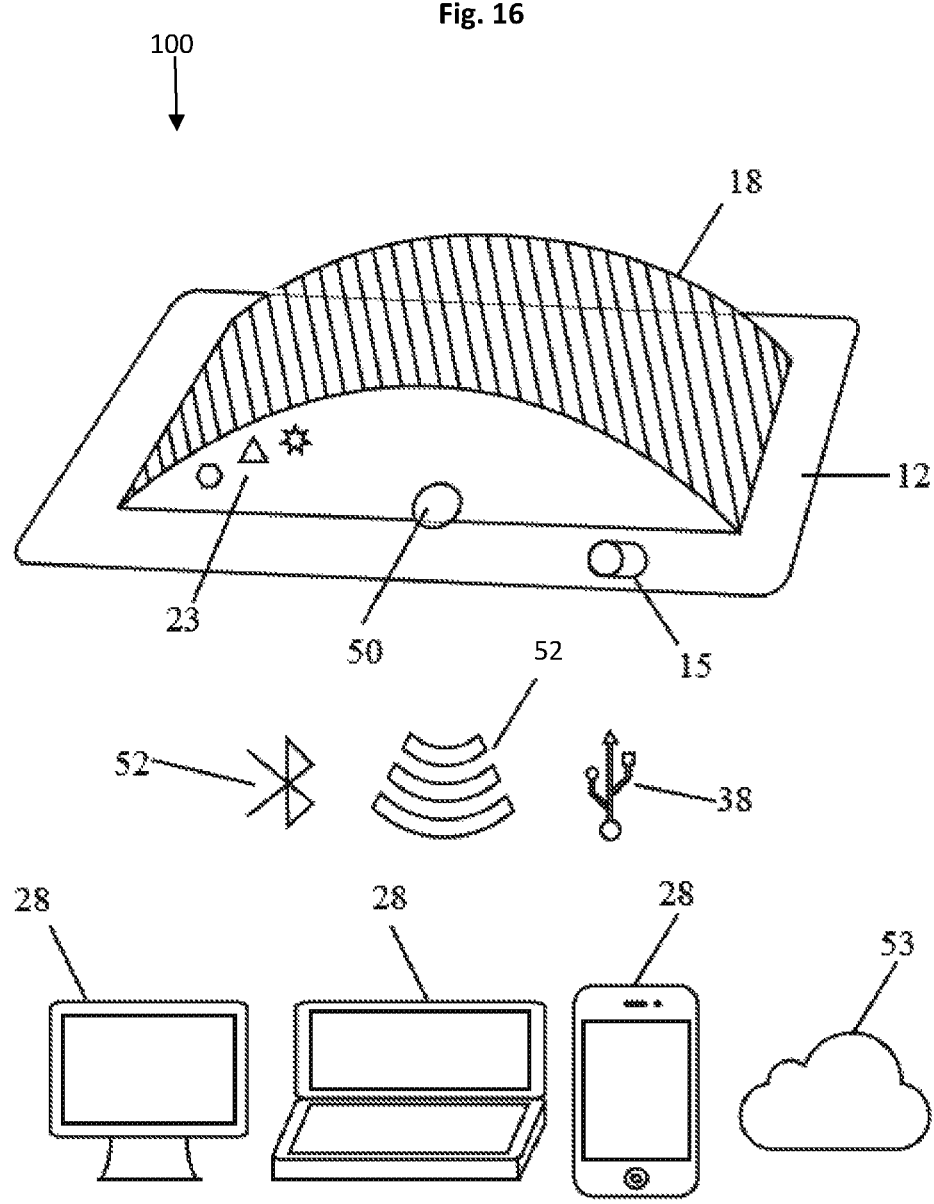
FIG. 16 is a drawing that illustrates a touch measurement apparatus according to an embodiment of the present invention used in clinical applications comprising multiple measurement sensors to monitor and record pressure, acceleration, torque, torsion, velocity, mass, force, friction, kinetic energy, tilt and position, and which also comprises software that allows the sensor data to be seen individually, as a data set or a single "value" that adds data collected on each individual sensor and produces an average that can be displayed.

Referring to FIG. 16, touch trainer 100 can be adapted for clinical uses. Preferably, touch trainer 100 comprises multiple force sensors 23 to monitor and record pressure, acceleration, torque, torsion, velocity, mass, force, friction, kinetic energy, tilt and position. Preferably, a remote display 28 allows data 26 from each force sensor 23 to be seen individually, as a data set or as a single "value" that adds data 26 collected on each individual force sensor 23 and produces an average that can be displayed. This is helpful when learning advanced techniques, manipulations and protocols that need to account for multiple sensor data points.

Figure 17:
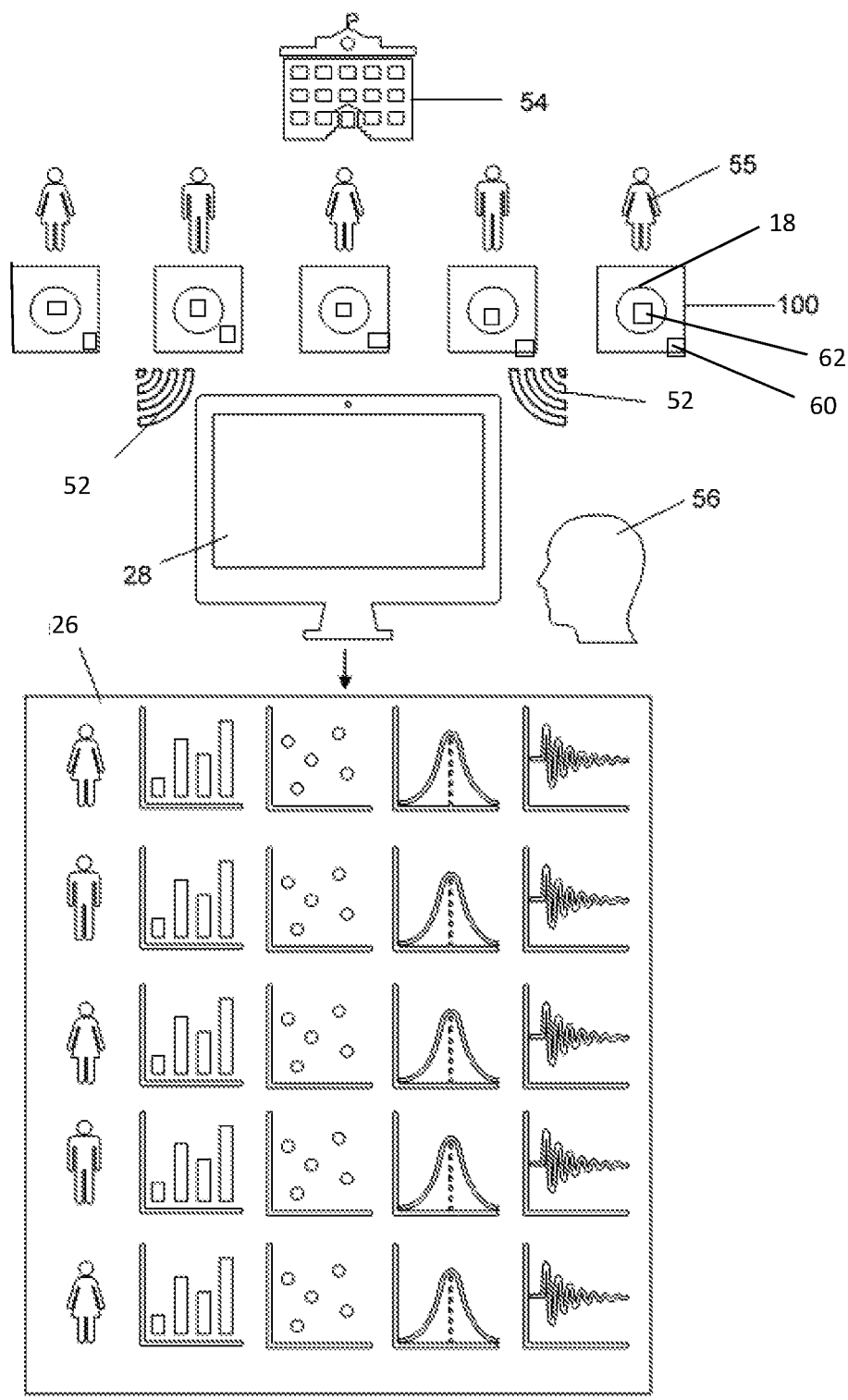
FIG. 17 is a drawing that illustrates how the data of multiple touch measurement apparatuses can be seen and monitored in a classroom setting by assigning a pad with a radio frequency identification chip to a trainee or student, according to an embodiment of the present invention.

Embodiments of touch trainer 100 can also be adapted for educational uses, for example as illustrated in FIG. 17 showing how multiple touch trainers 100 can be networked to create a training or educational experience. Preferably, a touch trainer 100 with an RFID chip 62 embedded within it is assigned to each student 55 within the educational program 54. Data 26 from each student's touch trainer 100 is transmitted to remote display 28 viewed by instructor 56 using software 57 capable of reporting individual use data 26.

Figure 18:
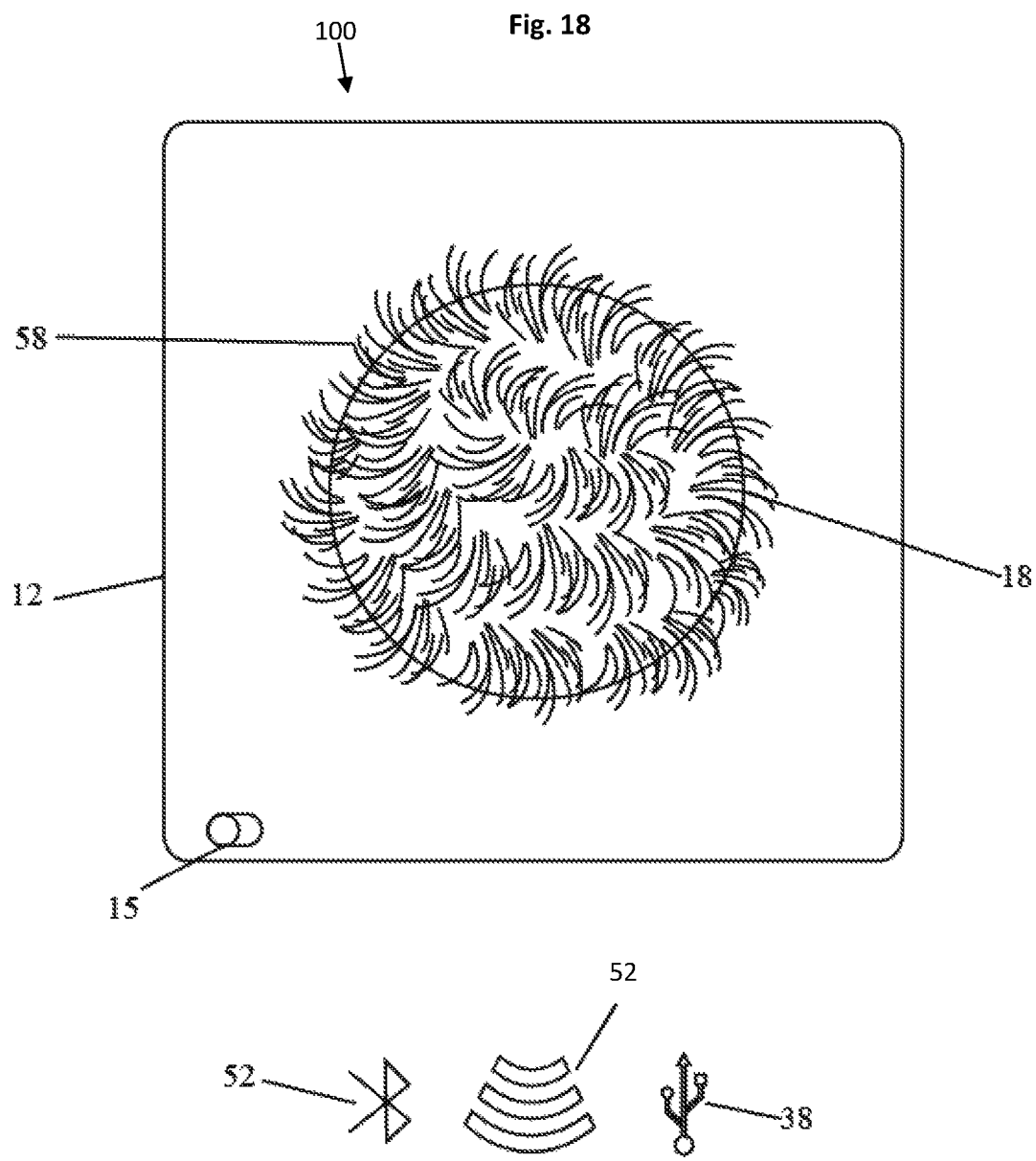
FIG. 18 is a drawing that illustrates a touch measurement apparatus according to an embodiment of the present invention used for veterinarian applications comprising hair or fur attached to the pad with an adhesive, multiple measurement sensors to monitor and record pressure, acceleration, torque, torsion, velocity, mass, force, friction, kinetic energy, tilt and/or position.
Figure 18:
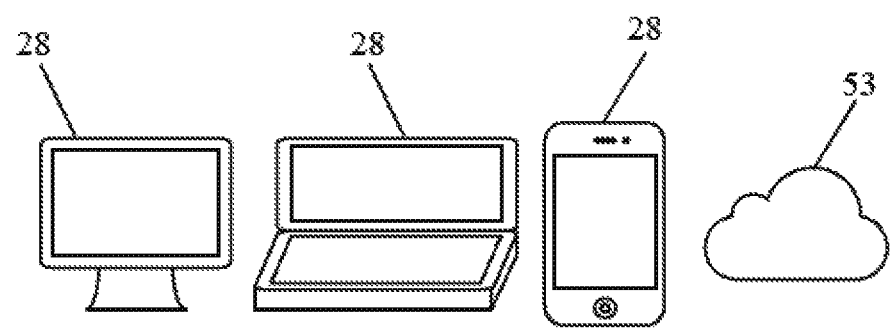

Embodiments of touch trainer 100 can also be adapted for veterinarian uses, one example of which is illustrated in FIG. 18. Preferably, touch trainer 100 comprises multiple force sensors 23 to monitor and record pressure, acceleration, torque, torsion, velocity, mass, force, friction, kinetic energy, tilt and position. Hair or fur 58 representative of whatever animal the user wishes to simulate is attached to pad 18 with an adhesive or can be overmolded, stitched, or blow-molded.

Figure 19:
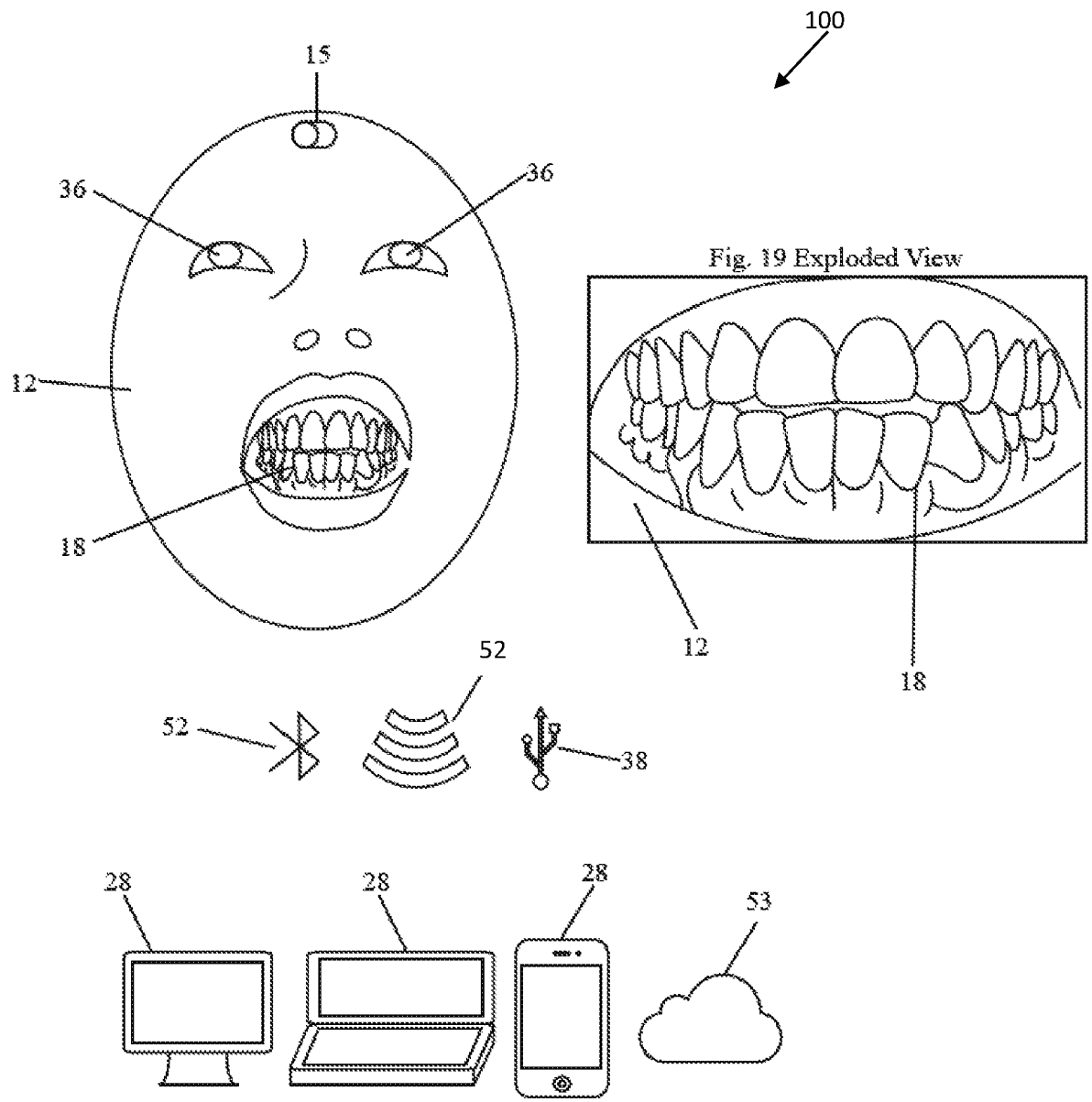
FIG. 19 is a drawing that illustrates a touch measurement apparatus according to an embodiment of the present invention used for dental applications comprising a mouth-shaped pad with two different Shore hardnesses, one hardness for gums and one hardness for teeth, and indicator lights in the eyes that glow red when too much pressure has been applied.

Embodiments of touch trainer 100 can also be adapted for dental uses, one example of which is illustrated in FIG. 19. Preferably, pad 18 takes the form of a human's mouth and teeth. To properly simulate the different Shore hardnesses of the gums and teeth, pad 18 is adapted to have one Shore hardness on the part of it representing teeth and a different Shore hardness on the part of it representing the gums. Touch trainer 100 can also include indicator lights 36 in the form of human eyes to glow a color such as red when too much pressure has been applied.

Figure 20:
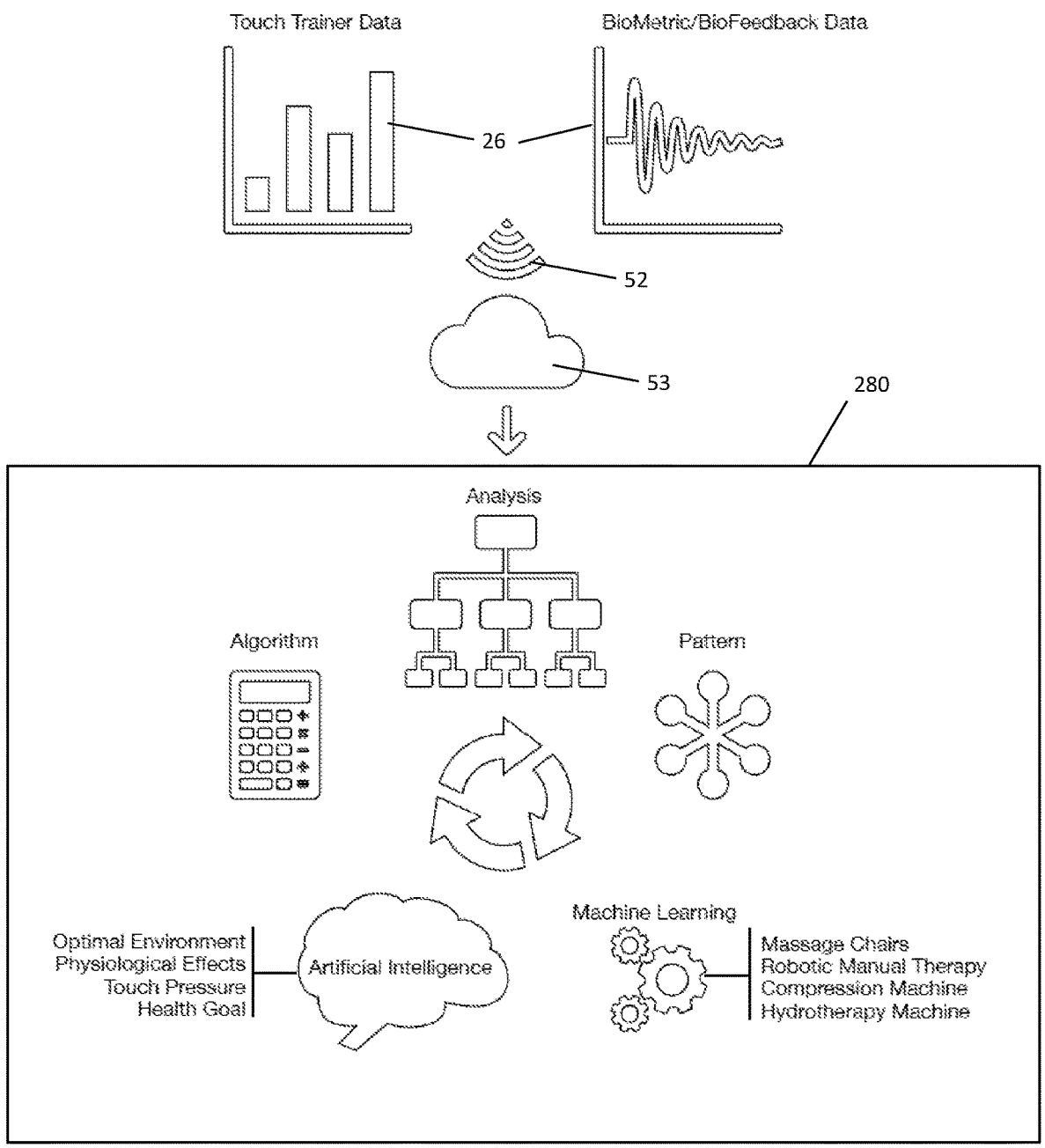
FIG. 20 is a drawing that illustrates the flow of data collected by a touch measurement apparatus according to an embodiment of the present invention, the data sent to a cloud-based application for applying analysis, patterns and algorithms, and allowing for artificially intelligent functions to drive or control other devices.
Figure 21A:
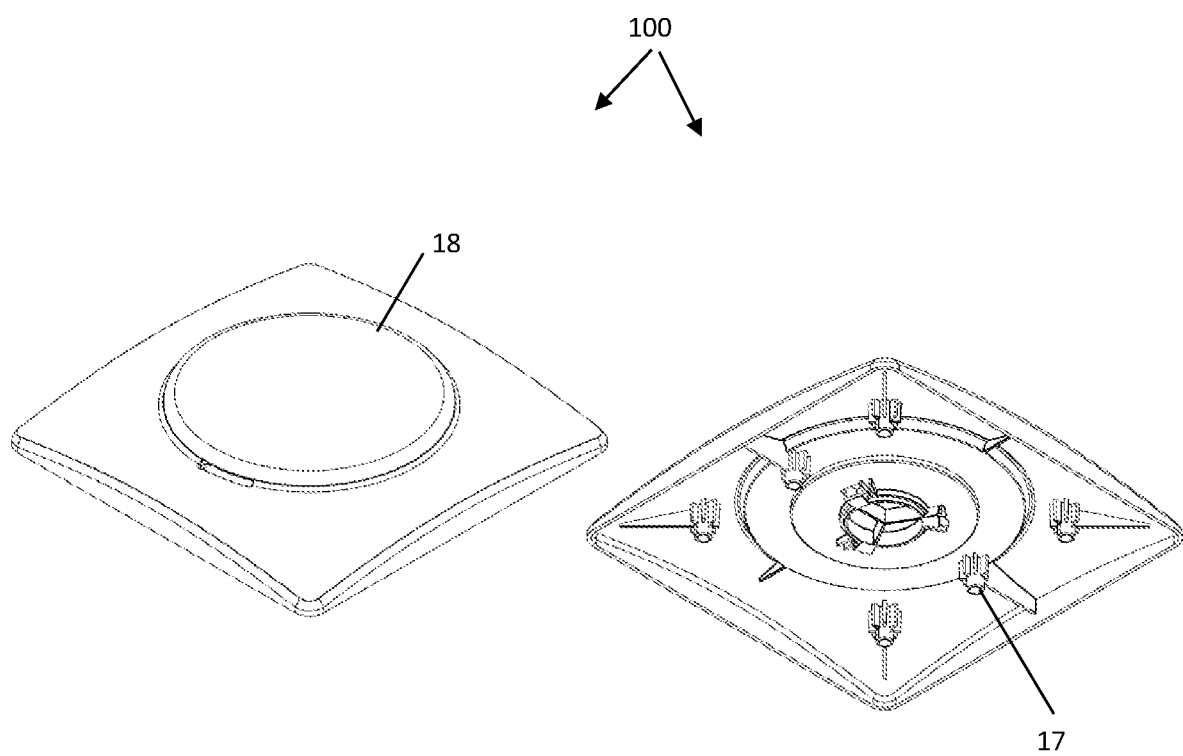
FIGS. 21A-21D is a set of drawings that illustrate various views of a touch measurement apparatus according to an embodiment of the present invention, FIG. 21A illustrating a perspective view from above and below, FIG. 21B illustrating a front view and a side view, FIG. 21C illustrating a cross-sectional side view, and FIG. 21D illustrating a top view and a bottom view.
Figure 21B:
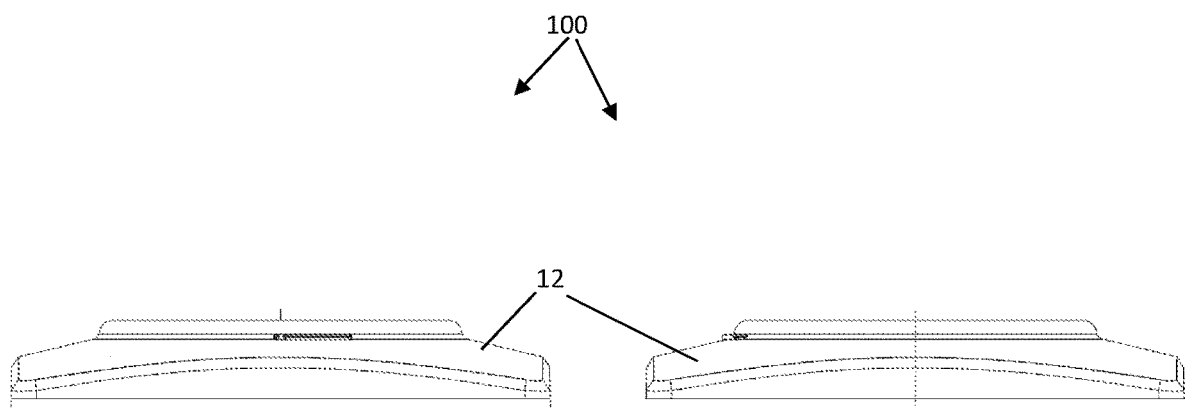
Figure 21C:
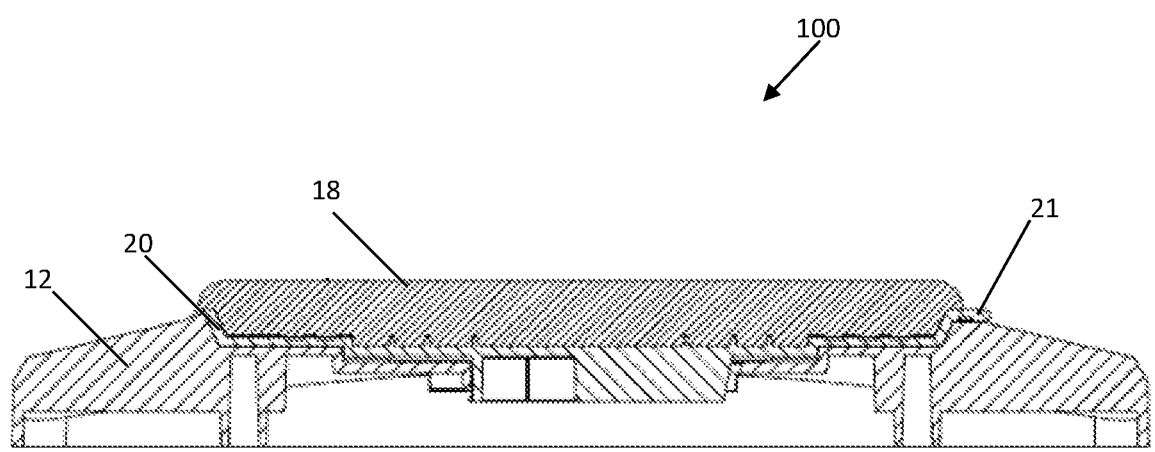
Figure 21D:
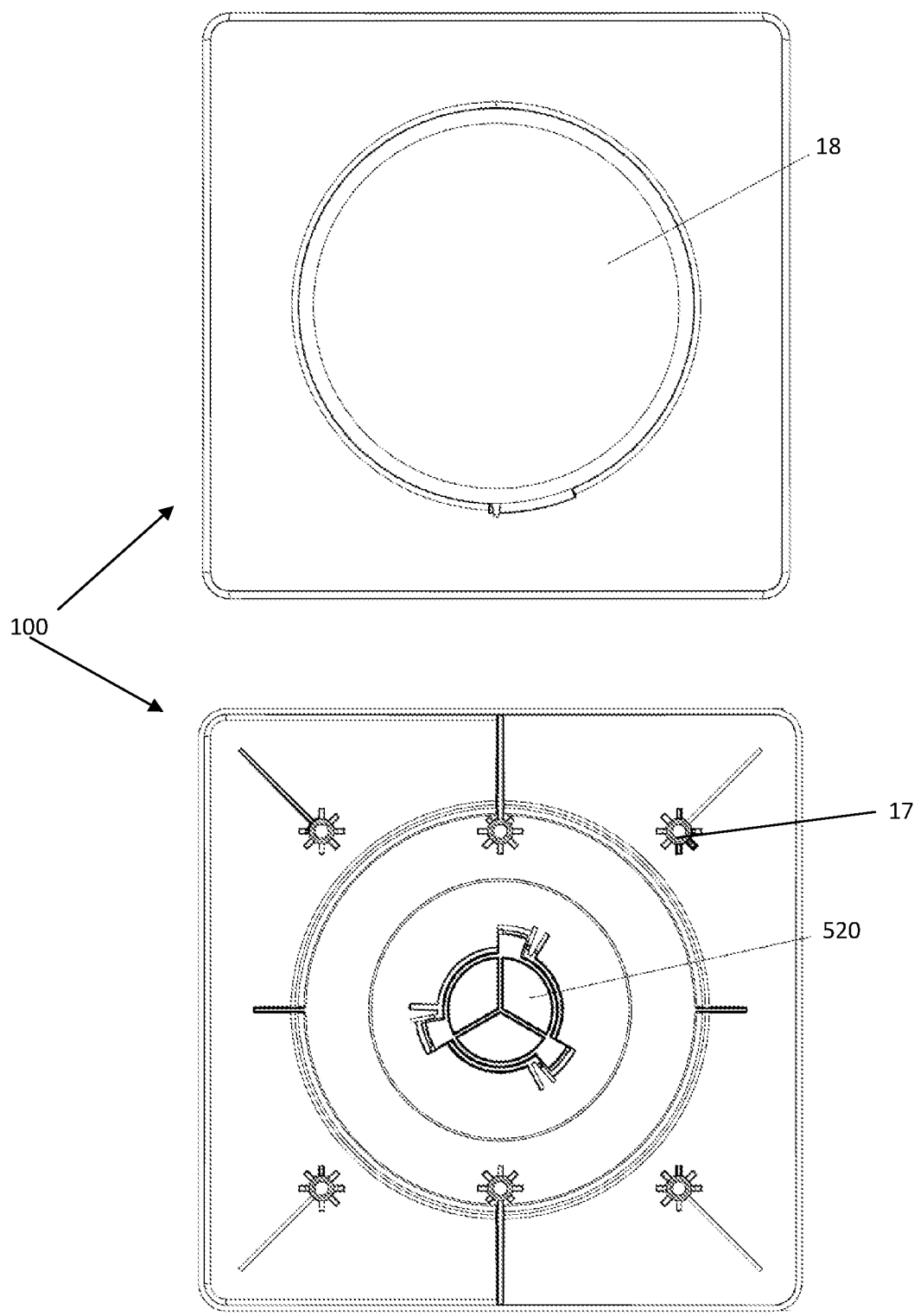

Embodiments of touch trainer 100 employ methods of networking and/or processing data 26, for example, as one embodiment of data flow is illustrated in FIG. 20. As described above, data 26 can include data created by force sensors 23 or any other type of data produced or collected by touch trainer 100. Preferably, data 26 is collected or logged by a touch trainer 100 and is transmitted, either through a wired connection 38 or wireless connection 52 or both, to cloud data storage 53. Software application 280 can then apply analysis, patterns, algorithms, machine learning, augment reality and/or artificial intelligence to data 26. Machine learning functions could coordinate with massage chairs, robotic manual therapy machines and/or methods, compression machines, hydrotherapy machines etc., for example by applying housing unit 24 comprising biosensors 30 to a person to obtain biosensor data and pressure data 26, and using the data 26 to drive the machine to provide the best outcome. Artificial intelligence functions could assist in determining or tracking optimal environments, physiological effects, touch pressure, health goals etc.

Embodiments of touch trainer 100 can be adapted to provide augmented reality. Augmented reality can be described as a direct or indirect live view of a physical, real-world environment, the elements of which are "augmented" by computer-generated perceptual information, preferably across multiple sensory modalities, including visual, auditory, haptic, somatosensory and olfactory. Preferably, embodiments of touch trainer 100 adapted to provide augmented reality do not have a simple display of data 26, but an integration of immersive sensations that are perceived for the particular application, for example, when working on a physiological condition. Augmented reality enhances remote collaboration, allowing students and instructors in different locales to interact by sharing a common virtual learning environment populated by virtual objects and learning materials. Preferably, users participate interactively and interact with knowledge more authentically and become active learners. Preferably, output display 11 includes optical projection systems, monitors, handheld devices, a head-mounted display ("HMD"), a head-up display ("HUD"), smart glasses and other devices. For example, in an embodiment of touch trainer 100 adapted to provide an augmented reality experience for use in treating conditions of the body like Lymphedema that cause tissue density variations, a picture of the physical condition is preferably augmented on or within pad 18, mimicking the actual condition that is being trained with superimposed anatomical structures and populated by virtual objects and learning materials such as text, graphics, video and audio. Force sensors 23 would preferably comprise sensors for pressure, acceleration, torque, torsion, velocity, mass, force, friction, kinetic energy, tilt and position.

Various exercises can be developed using touch trainer 100. In one such exercise, pressure ranges measured by force sensors 23 appear on display 11 and the user applies a pressure to pad 18 that the user believes is the correct amount of pressure to apply for that particular application. The exercise is preferably conducted for at least about two minutes and the accuracy is calculated and displayed on display 11 upon conclusion of the exercise, and can be emailed to the user or transmitted to software application 280 for ranking or other processing. In this way, users in an organization can be assessed.

Companies that sell products to consumers, have products used in massage, spa manual therapy, and/or train in massage, spa, manual therapy, can use an Application Programming Interface that allows the touch training device application and their company applications to talk to each other. Then they can train and verify in a mobile way.

Touch trainer 100 can be adapted for organizational, presentation or survey uses as well, for example, at tradeshows or conferences. Touch trainer 100 can comprise a scanner 510 to scan a code such as a QR code on a user's conference/trade show tag or card to identify the user and associate data 26 with that user. Optionally, output display 11 can be an external display like a tablet or TV monitor to allow for public viewing. Once the user scans their code on touch trainer 100, overview instructions are displayed on display 11, the user performs an exercise, optionally introduced with a practice exercise, and resulting data 26 is displayed, stored and/or transmitted.

The global health community is impacted by chronic stress, chronic pain and mobility issues that reduce the quality of life and work function for people and are burdening the healthcare system. Those that fall into higher socioeconomic status have the ability to seek out adjunct therapy services to reduce the impact of these conditions and reduce the comorbidity diseases that accompany them. But the manual therapy treatments they are receiving are subjectively delivered leading to inconsistent results. Many families don't have the disposable income to pay for services and those residing in rural areas have limited access to services. There is significant time wasted in transporting a person to and from therapy. Many patients do not have the opportunity to receive the therapy services that could now be provided effectively in the home with standard of care outcomes using the touch trainer 100.

Optionally, embodiments of the present invention can include a general or specific purpose computer or distributed system programmed with computer software implementing steps described above, which computer software may be in any appropriate computer language, including but not limited to C++, FORTRAN, BASIC, Java, Python, Linux, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements. One or more processors and/or microcontrollers can operate via instructions of the computer code and the software is preferably stored on one or more tangible non-transitive memory-storage devices.

Embodiments of the present invention provide a technology-based solution that overcomes existing problems with the current state of the art in a technical way to satisfy an existing problem for users of touch training devices. An embodiment of the present invention is necessarily rooted in computer technology in order to overcome a problem specifically arising in the realm of computers. Embodiments of the present invention achieve important benefits over the current state of the art, such as increased efficiency in using data, better quality analysis of data, increased flexibility and faster data acquisition.

Note that in the specification and claims, "about" or "approximately" means within twenty percent (20%) of the numerical amount cited. As used herein, the singular forms "a," "an," and "the" include plural referents unless the context clearly dictates otherwise. Thus, for example, reference to "a functional group" refers to one or more functional groups, and reference to "the method" includes reference to equivalent steps and methods that would be understood and appreciated by those skilled in the art, and so forth. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and and/or reconfiguration of their relationships with one another.

What is claimed is:

1. A manual force measurement apparatus comprising:
   a base;
   a pad disposed on said base comprising a material that simulates human or animal body tissue;
   said pad comprising a pocket for receiving an ice pack; and
   at least one sensor configured to receive a force applied by a person, said at least one sensor capable of generating output data related to the force.

2. The apparatus of claim 1 further comprising a display for displaying said output data.

3. The apparatus of claim 2 wherein said display comprises a device selected from the group consisting of optical projection system, monitor, handheld computing device, head-mounted display, head-up display, and smart glasses.

4. The apparatus of claim 1 wherein said pad is removeable from said base.

5. The apparatus of claim 1 wherein said pad comprises materials having different hardnesses.

6. The apparatus of claim 5 wherein at least one of said materials comprises at least one object selected from the group consisting of beads, marbles, spheres, strips and tubes.

7. The apparatus of claim 1 wherein said pad comprises a material having a lower freezing point than water.

8. The apparatus of claim 1 wherein said pad comprises a shape selected from the group consisting of an anatomical body part of a human or animal, a sphere, a square, and a triangle.

9. The apparatus of claim 1 wherein said pad comprises a pressure-sensitive conductive sheet.

10. The apparatus of claim 1 further comprising a radio frequency identification reader or an identification card scanner.

11. The apparatus of claim 1 further comprising a recognition device for recognizing a fingerprint or personal identification number.

12. The apparatus of claim 1 further comprising a wireless connection between said at least one sensor and said base.

13. The apparatus of claim 1 further comprising a wireless transmitter for transmitting said output data.

14. A method of measuring a manual force, the method comprising:
    a pad receiving a manually applied force, wherein the pad comprises a material that simulates human or animal body tissue;
    generating data related to the applied force using at least one sensor;
    performing the receiving and generating steps at the beginning of a time period;
    repeating the receiving and generating steps at the end of a time period; and
    comparing the data from each time period.

15. The method of claim 14 further comprising displaying the data.

16. The method of claim 14 further comprising storing the data.

17. The method of claim 14 further comprising producing a sound or visual effect when a predetermined force is applied.

18. The method of claim 14 further comprising transmitting the data to another device or network.

19. The method of claim 14 further comprising associating a value of the applied force with a preexisting standard or protocol.

20. The method of claim 14 further comprising indicating whether or not the force is within a predetermined range.

21. The method of claim 14 further comprising disposing an ice pack on or within the pad and freezing the pad.

22. The method of claim 14 further comprising identifying an individual user of the pad.

23. A method of defining a standard or protocol for training and/or performing touch manipulations, the method comprising:
    attaching a biosensor to a person;
    applying different forces to the person using an algometer;
    obtaining data from the biosensor during the applying step;
    determining a range of forces that produce a desired effect in the person as measured by the data; and
    using the range of forces to establish a standard or protocol to produce the desired effect.

24. The method of claim 23 wherein the desired effect comprises an effect selected from the group consisting of parasympathetic nervous system response, reflexive effect, fluid exchanges in soft tissue, mechanical effect, and relaxation effect.

25. The method of claim 23 wherein the standard or protocol is established based on data obtained from performing the attaching, applying, obtaining, and determining steps on a plurality of persons.

26. The method of claim 23 further comprising:
instructing a user to apply a force to a pad, wherein the pad comprises material that simulates human or animal body tissue and wherein the pad generates user force data using at least one sensor;
comparing the user force data to the standard or protocol; and
repeating the instruction step until the user has satisfied a predetermined accuracy related to the standard or protocol.

27. A method of using biosensors to control environmental conditions, the method comprising:
attaching a biosensor to a person;
obtaining data from the biosensors, the data based on a force applied by a provider to the person's body;
displaying the data to the provider so the provider can adjust the force applied to the person, wherein the provider is a manual or massage therapist and wherein the method is used as an adjunctive or diagnostic tool; and
using the data to adjust an environmental condition.

28. The method of claim 27 wherein the environmental condition is selected from the group consisting of: temperature of a room, temperature of a table, room light intensity, room light color, sound volume, music selection, aromatherapy type, and aromatherapy intensity.

29. The method of claim 27 wherein the environmental condition is automatically adjusted based on the data.

30. A method of measuring a manual force, the method comprising:
disposing an ice pack within a pad and freezing the pad;
the pad receiving a manually applied force, wherein the pad comprises a material that simulates human or animal body tissue; and
generating data related to the applied force using at least one sensor.

31. The method of claim 30 further comprising displaying the data.

32. The method of claim 30 further comprising storing the data.

33. The method of claim 30 further comprising producing a sound or visual effect when a predetermined force is applied.

34. The method of claim 30 further comprising transmitting the data to another device or network.

35. The method of claim 30 further comprising associating a value of the applied force with a preexisting standard or protocol.

36. The method of claim 30 further comprising indicating whether or not the force is within a predetermined range.

37. The method of claim 30 further comprising identifying an individual user of the pad.

* * * * *